United States Patent
Farokhnia et al.

(10) Patent No.: US 12,005,159 B2
(45) Date of Patent: Jun. 11, 2024

(54) CONFORMAL, NON-OCCLUDING SENSOR ARRAY FOR CARDIAC MAPPING AND ABLATION

(71) Applicant: CORNELL UNIVERSITY, Ithaca, NY (US)

(72) Inventors: Nazanin Farokhnia, New York, NY (US); Alexandre Caprio, New York, NY (US); Varun Umesh Kashyap, New York, NY (US); Subhi Al' Aref, New York, NY (US); Bobak Mosadegh, New York, NY (US); James K. Min, New York, NY (US); Simon Dunham, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 81 days.

(21) Appl. No.: 17/774,440

(22) PCT Filed: Nov. 6, 2020

(86) PCT No.: PCT/US2020/059452
§ 371 (c)(1),
(2) Date: May 4, 2022

(87) PCT Pub. No.: WO2021/092416
PCT Pub. Date: May 14, 2021

(65) Prior Publication Data
US 2022/0387675 A1 Dec. 8, 2022

Related U.S. Application Data

(60) Provisional application No. 63/015,344, filed on Apr. 24, 2020, provisional application No. 62/932,192, filed on Nov. 7, 2019.

(51) Int. Cl.
*A61B 18/14* (2006.01)
*A61L 29/08* (2006.01)
(Continued)

(52) U.S. Cl.
CPC ............... *A61L 29/16* (2013.01); *A61L 29/08* (2013.01); *A61B 2018/0022* (2013.01)

(58) Field of Classification Search
CPC ...................................... A61B 18/14
See application file for complete search history.

(56) References Cited

U.S. PATENT DOCUMENTS 5,345,936 A * 9/1994 Pomeranz ............ A61B 5/6853
600/374
5,904,680 A * 5/1999 Kordis ................. A61B 5/6858
606/41

(Continued)

OTHER PUBLICATIONS

International Preliminary Report on Patentability on PCT PCT/US2020/059452 dated May 19, 2022.
(Continued)

*Primary Examiner* — Cachet I Proctor
(74) *Attorney, Agent, or Firm* — FOLEY & LARDNER LLP

(57) ABSTRACT

Systems, methods, and devices having improved conformal properties for biomedical signal measurement are disclosed. A device can have a first polymer substrate coupled to a conductive layer forming a conductive trace electrically coupled to a conductive pad exposed via an opening. The device can have a second polymer substrate forming a first cavity between the first polymer substrate and the second polymer substrate. The device can have a first inlet portion that receives a fluid that expands the first cavity causing the device to conform to an anatomical structure. The structure can be an atrium, such as the left atrium, of the heart of a patient. The device can conform to the walls of the tissue (Continued)

structure, and the conductive pad exposed via the opening can detect a signal from the wall of the tissue structure. The signal can be provided to an external measurement device for processing.

15 Claims, 28 Drawing Sheets

(51) Int. Cl.
*A61L 29/16* (2006.01)
*A61B 18/00* (2006.01)

(56) References Cited

U.S. PATENT DOCUMENTS

| | | | |
|---|---|---|---|
| 6,115,626 A * | 9/2000 | Whayne | A61B 5/287 600/523 |
| 9,545,216 B2 | 1/2017 | D'Angelo et al. | |
| 9,757,050 B2 | 9/2017 | Ghaffari et al. | |
| 11,559,225 B1 * | 1/2023 | Lee | A61B 5/0531 |
| 11,642,064 B2 * | 5/2023 | Sterrett | A61B 18/1492 600/374 |
| 11,878,095 B2 * | 1/2024 | Beeckler | A61M 25/0136 |
| 2003/0086206 A1 | 5/2003 | Kube et al. | |
| 2004/0167509 A1 | 8/2004 | Taimisto | |
| 2006/0211191 A1 | 9/2006 | Sabev | |
| 2008/0004679 A1 * | 1/2008 | Naghavi | A61N 2/006 607/108 |
| 2008/0140072 A1 * | 6/2008 | Stangenes | A61B 18/14 606/41 |
| 2008/0314867 A1 | 12/2008 | Woychik et al. | |
| 2009/0203962 A1 | 8/2009 | Miller et al. | |
| 2010/0204560 A1 * | 8/2010 | Salahieh | A61B 5/01 606/41 |
| 2011/0274829 A1 | 11/2011 | Feurer et al. | |
| 2012/0126460 A1 | 5/2012 | Shin et al. | |
| 2013/0267081 A1 | 10/2013 | Fox et al. | |
| 2014/0268780 A1 | 9/2014 | Wang et al. | |
| 2015/0177886 A1 | 6/2015 | Gorsica et al. | |
| 2015/0366508 A1 | 12/2015 | Chou et al. | |
| 2015/0373831 A1 | 12/2015 | Rogers et al. | |
| 2016/0165719 A1 | 6/2016 | Li et al. | |
| 2016/0353978 A1 * | 12/2016 | Miller | A61B 1/00096 |
| 2017/0040306 A1 | 2/2017 | Kim et al. | |
| 2017/0136496 A1 | 5/2017 | Jacobs et al. | |
| 2017/0333124 A1 * | 11/2017 | Gelbart | A61B 5/065 |
| 2018/0067003 A1 | 3/2018 | Michiwaki | |
| 2018/0068759 A1 | 3/2018 | Bihler et al. | |
| 2018/0200524 A1 | 7/2018 | Toth et al. | |
| 2018/0343741 A1 | 11/2018 | Williams et al. | |
| 2019/0030710 A1 | 1/2019 | Lessing et al. | |

OTHER PUBLICATIONS

International Search Report and Written Opinion on PCT PCT/US2020/059452 dated Mar. 23, 2021.
International Search Report and Written Opinion on PCT PCT/US2021/028940 dated Oct. 22, 2021.
Lin et al. "Design and fabrication of stretchable multilayer self-aligned interconnects for flexible electronics and large-area sensor arrays using excimer laser photoablation" IEEE Electron Device Letters, vol. 30, No. 1, Jan. 2009, retrieved from <https://ieeexplore.ieee.org/abstract/document/4703248>.
International Preliminary Report on Patentability for PCT/US2021/028940 dated Nov. 3, 2022.

* cited by examiner

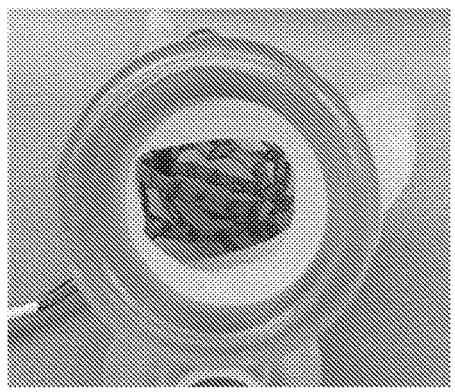
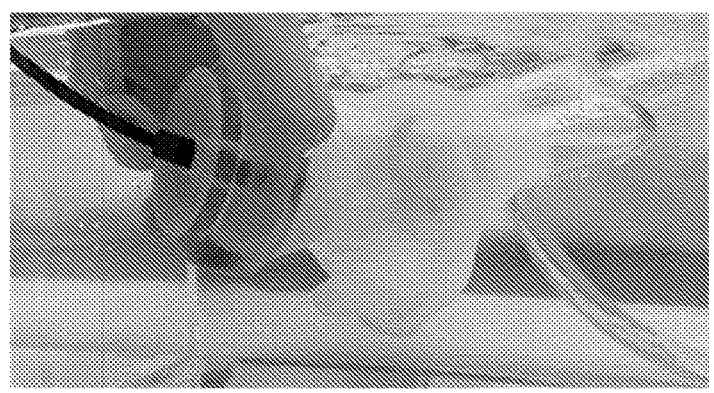
FIG. 11A  FIG. 11B
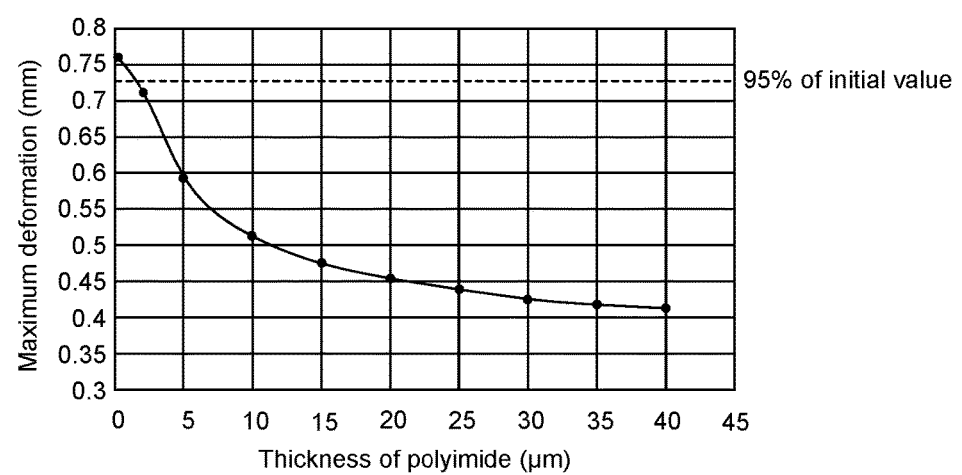
FIG. 11C

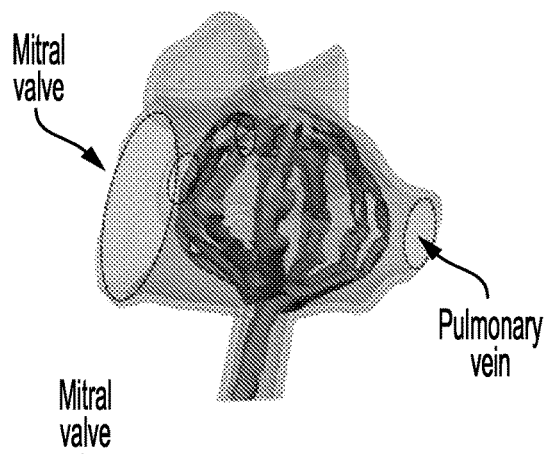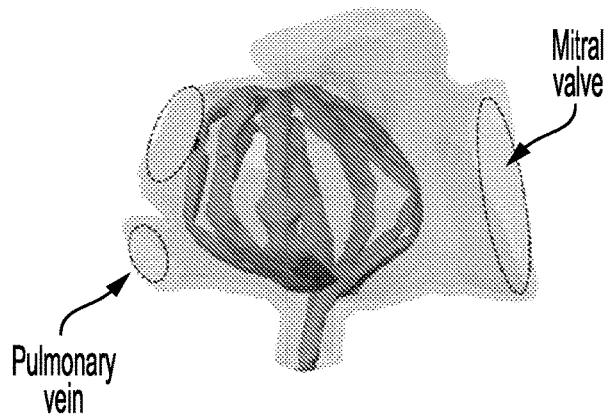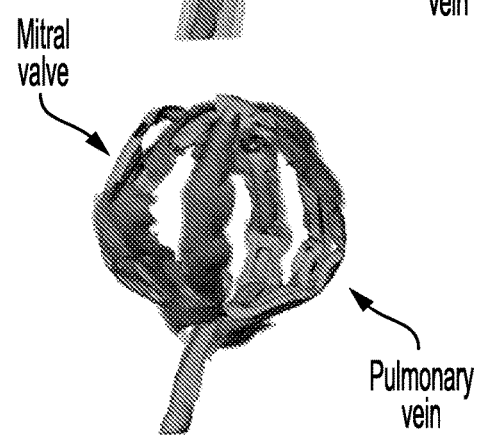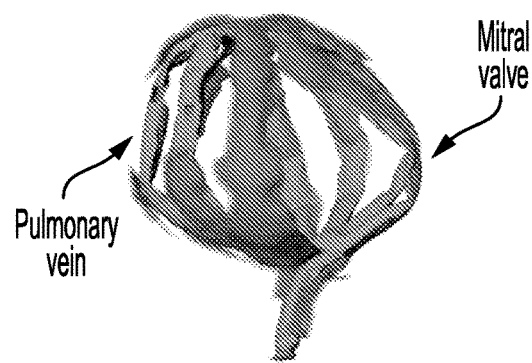
FIG. 24A    FIG. 24B

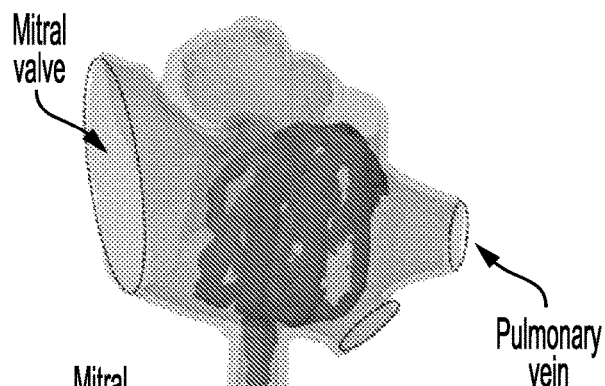
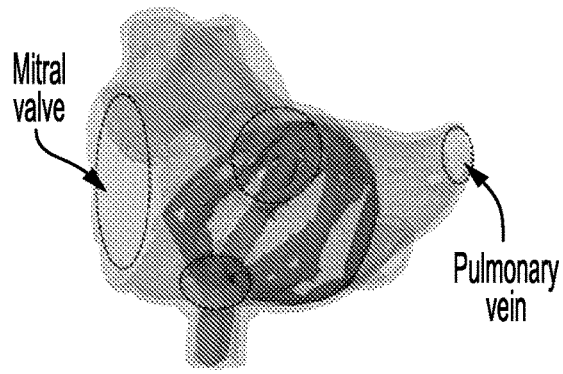
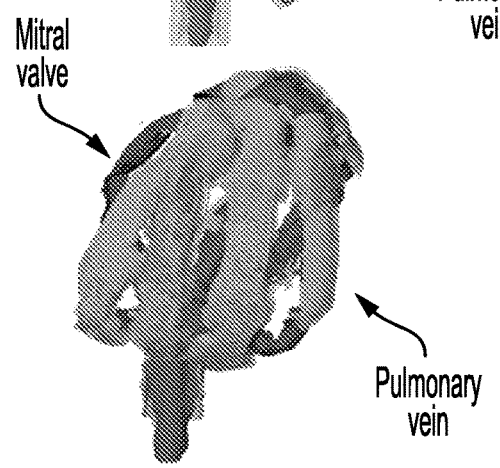
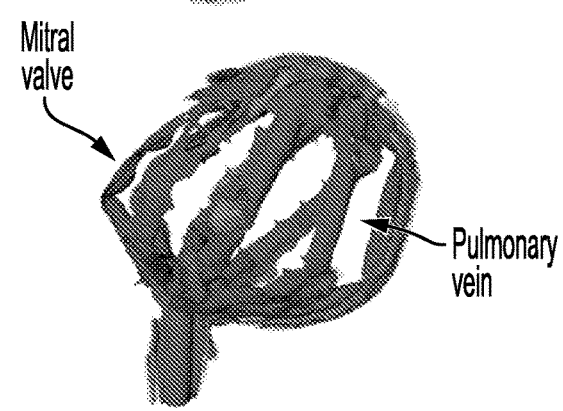
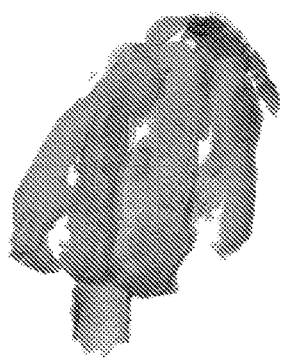
FIG. 26A     FIG. 26B

CONFORMAL, NON-OCCLUDING SENSOR ARRAY FOR CARDIAC MAPPING AND ABLATION

CROSS-REFERENCES TO RELATED APPLICATIONS

This application is a U.S. National Phase Application Under 35 U.S.C. § 371 of International Application No. PCT/US2020/059452, filed on Nov. 6, 2020, and claims the benefit of and priority to U.S. Provisional Patent Application No. 62/932,192, entitled "CONFORMAL, NON-OCCLUDING SENSOR ARRAY FOR CARDIAC MAPPING AND ABLATION," filed Nov. 7, 2019; and claims the benefit of and priority to U.S. Provisional Patent Application No. 63/015,344, entitled "CATHETER-DEPLOYABLE SOFT ROBOTIC SENSOR ARRAYS AND PROCESSING OF FLEXIBLE CIRCUITS," filed Apr. 24, 2020; the contents of each of which are hereby incorporated by reference in their entireties.

STATEMENT REGARDING FEDERALLY SPONSORED RESEARCH

This invention was made with government support under contract no. W81XWH-18-1-0201 awarded by the Department of Defense. The government has certain rights in the invention.

BACKGROUND

Having knowledge of specific internal organ structure can be vital in providing treatment to patients. However, mapping the internal structures of organs is not practicable using conventional sensors in part because they do not conform to the internal structure of a desired organ. Further, it can be challenging to position sensors inside of an organ in a way that does not occlude the flow of blood or other fluids inside the organ.

SUMMARY

In various potential embodiments, the systems and methods of this technical solution solve the aforementioned issues by providing catheter deployable, soft robotic sensor arrays that can be actuated to conform to an anatomical structure such as an internal organ, such as the atrium of the heart. Sensors with flexible circuitry can be embedded in the outer surface of the soft robotic device. The sensor array can be embedded in a three-dimensional (3D) printed balloon catheter, which can be introduced to the body using a surgical technique. After insertion, the balloon catheter device can be actuated, and expand to conform to the structure of the internal organ. Conforming to the structure of an organ or other anatomical structure allows for more precise mapping or sensing of signals generated by the organ. Different geometric configurations can be provided for different anatomical configurations.

At least one aspect of the present disclosure is directed to a device with improved structural conformity. The device can include a first polymer (or otherwise biologically-inert) substrate having a first surface (e.g., an inner surface of the device) coupled to a conductive (e.g., metallic) layer forming a conductive trace. The conductive trace can be electrically coupled to a conductive pad that is exposed through a second surface (e.g., an outer surface of the device that may make contact with tissue) of the first polymer substrate via an opening. The device can include a second polymer (or otherwise biologically-inert) substrate forming a first cavity between the first polymer substrate and the second polymer substrate. The device can include a first inlet portion that receives a fluid that expands (e.g., inflates) the first cavity causing the device to at least partially conform to an anatomical structure. The conductive pad can detect a signal from the anatomical structure.

In some implementations, the first polymer substrate, the second polymer substrate, and the first inlet portion can form a first soft-electronic beam of a plurality of soft-electronic beams. In some implementations, the plurality of soft-electronic beams can form a three-dimensional (3D) structure that conforms to the anatomical structure responsive to receiving the fluid. In some implementations, the first polymer or the second polymer can include at least one of a urethane polymer, a polyurethane polymer, a copolymer, a silicone polymer, or an elastomer. In some implementations, the conductive trace can provide the signal detected by the conductive pad to a catheter that transmits the signal to an external measurement device.

In some implementations, the three-dimensional structure formed by the plurality of soft-electronic beams can form at least one of a star configuration, a sphere configuration, a linear configuration, a conical configuration, or a cylindrical configuration. In some implementations, the conductive trace can be coupled to a portion of a flexible printed-circuit board substrate that is coupled to at least one of the first polymer substrate or the second polymer substrate. In some implementations, the conductive pad can be coupled to a sensor comprising at least one of a force sensor, a shear sensor, an ultrasound senor, a thermal sensor, a position sensor, an electrocardiogram sensor, or an electrochemical sensor.

In some implementations, the sensor is coupled to at least one of the first polymer substrate, the second polymer substrate, or a flexible printed-circuit board layer coupled to the conductive layer and to at least one of the first polymer substrate or the second polymer substrate. In some implementations, the second polymer substrate is coupled to a second conductive trace electrically coupled to a second conductive pad; and wherein the second conductive pad is coupled to a second sensor comprising at least one of a force sensor, a shear sensor, an ultrasound senor, a thermal sensor, a position sensor, an electrocardiogram sensor, or an electrochemical sensor. In some implementations, the conductive trace is patterned in a serpentine pattern that is capable of stretching in response to the first inlet portion receiving the fluid that expands the first cavity.

At least one other aspect of the present disclosure is directed to a system. The system can include a lumen configured to provide a fluid from a fluid reservoir. The system can include an expandable measurement device having a plurality of beams. Each of the plurality of beams can have a first end, a second end, and a cavity portion. The first end of the plurality of beams can be coupled to the lumen and receive the fluid from the fluid reservoir to fill the cavity portion. The system can include a plurality of electrodes disposed on a first surface of each of the plurality of beams. The system can include a plurality of transmission lines. Each of the plurality of transmission lines can be electrically coupled to a respective one of the plurality of electrodes. The plurality of transmission lines may be part of a catheter device.

In some implementations, the second end of each the plurality of beams is fluidly coupled to one another at one or more junctions. In some implementations, different amounts of fluid provided by the lumen causes the cavity portions of each of the plurality of beams to expand by varying degrees to conform to different tissue or other anatomical structures. In some implementations, each of the plurality of beams includes a substrate comprising at least one of a urethane polymer, a polyurethane polymer, a copolymer, a silicone polymer, or an elastomer. In some implementations, the plurality of electrodes each detect a signal from one or more surfaces of a tissue structure; and wherein the transmission lines transmit the signals detected from each of the plurality of electrodes to an external measurement device through wired or wireless means.

At least one other aspect of the present disclosure is directed to a method of detecting signals using an expandable measurement device. The method can include positioning a measurement device within an internal tissue or other anatomical structure of a patient. The measurement device can include a first polymer substrate having a first surface coupled to a conductive (e.g., metallic) layer forming a conductive trace electrically coupled to a conductive pad exposed through a second surface of the first polymer substrate via an opening. The measurement device can include a second polymer substrate forming a first cavity between the first polymer substrate and the second polymer substrate. The measurement device can include a first inlet portion coupled to a lumen that receives a fluid that expands the first cavity. The method can include providing, via the lumen, a first amount of the fluid that causes the measurement device to expand by an amount corresponding to the first amount of fluid. The conductive pad can detect a signal from the internal tissue structure via the opening responsive to expanding the first cavity. The method can include monitoring, responsive to providing the first amount of the fluid via the lumen, using a measurement device, the signal detected by the conductive pad.

In some implementations, the method can include determining that the signal from the internal tissue structure is not detected by the conductive pad responsive providing the first amount of the fluid. In some implementations, the method can include providing, responsive to the determination that the signal is not detected, a second amount of the fluid that causes the cavity to a size larger than the size of the cavity after providing the first amount of the fluid. In some implementations, monitoring the signal using the measurement device can include measuring at least one of a force value, a shear force value, an ultrasound value, a temperature value, a position value, an electrocardiogram value, or an electrochemical value. In some implementations providing the first amount of fluid can include determining the first amount of the fluid based on at least one of a type of the internal tissue structure, a volume of the measurement device, or information from an image of the internal tissue structure. In some implementations, the internal tissue structure is an atrium of a heart of the patient, and wherein positioning the measurement device within the internal tissue structure is performed using at least a transseptal puncture.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. Aspects can be combined and it will be readily appreciated that features described in the context of one aspect of the invention can be combined with other aspects. Aspects can be implemented in any convenient form. For example, by appropriate computer programs, which can be carried on appropriate carrier media (computer readable media), which can be tangible carrier media (e.g. disks) or intangible carrier media (e.g. communications signals). Aspects can also be implemented using suitable apparatus, which can take the form of programmable computers running computer programs arranged to implement the aspect. As used in the specification and in the claims, the singular form of 'a', 'an', and 'the' include plural referents unless the context clearly dictates otherwise.

BRIEF DESCRIPTION OF THE DRAWINGS

The accompanying drawings are not intended to be drawn to scale, unless specifically indicated in a particular drawing. Like reference numbers and designations in the various drawings indicate like elements. For purposes of clarity, not every component can be labeled in every drawing. In the drawings:

FIGS. 11A and 11B depict views of example balloon catheters disposed within left atrium models, in accordance with one or more potential implementations;

FIG. 11C depicts example experimental data of maximum deformation of a balloon actuator versus the thickness of polyimide, in accordance with one or more potential implementations;

FIGS. 24A and 24B depict example conformability analyses of soft-robotic sensor arrays deployed in patient-specific 3D printed left atria, in accordance with one or more potential implementations;

FIGS. 26A and 26B depict additional example conformability analyses of soft-robotic sensor arrays deployed in patient-specific 3D printed left atria, in accordance with one or more potential implementations;

DETAILED DESCRIPTION

Figure 1:
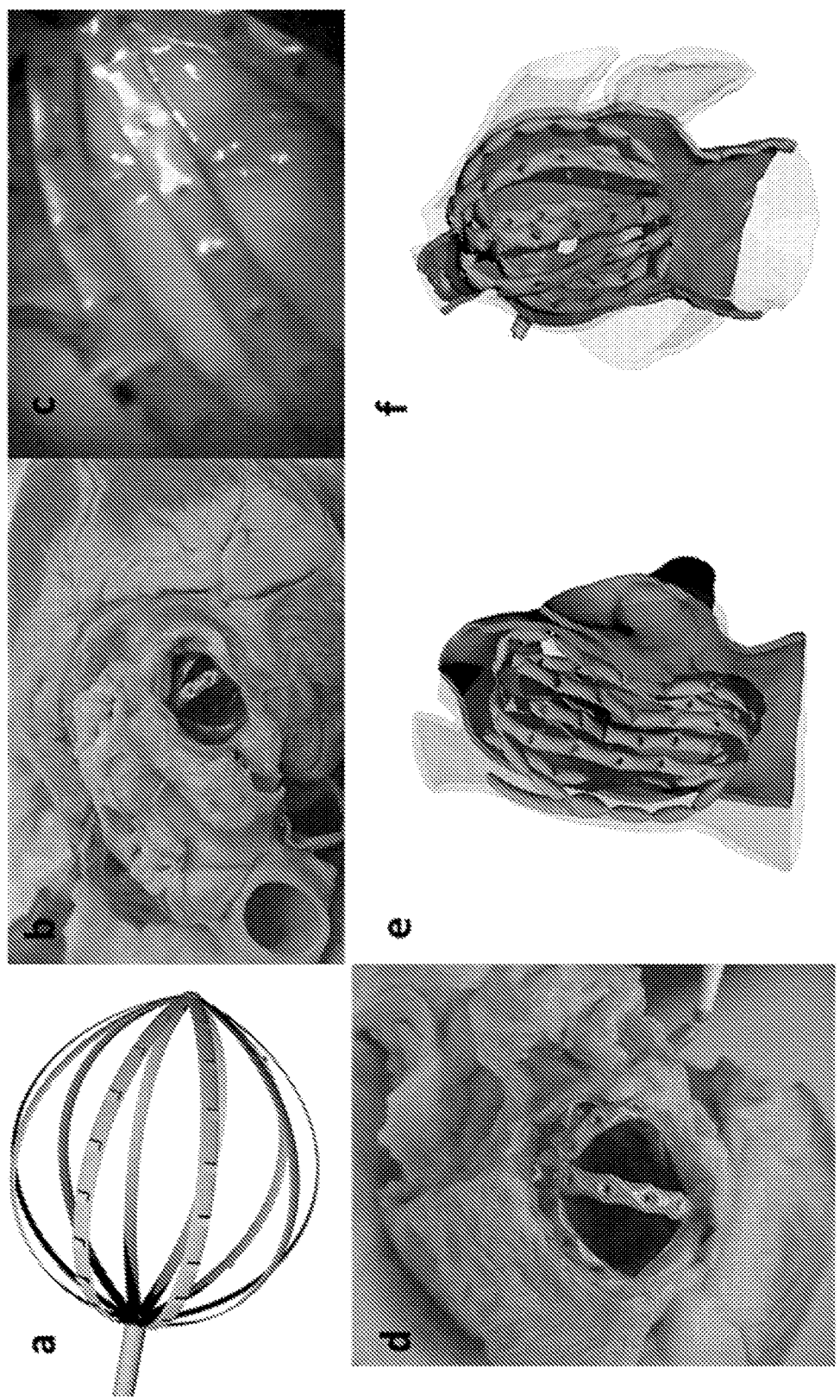
FIG. 1 depicts various views of an example balloon catheter used for mapping the structure of an atria of the heart, in accordance with one or more potential implementations.

For the purposes of reading the description of the various implementations and techniques described herein, the following brief descriptions of the sections of the Specification may be helpful.

Section A describes implementations of a catheter deployable soft-robotic inflatable basket for enhanced conformability to the left atrium of the heart.

Section B describes implementations for multilayer fabrication of durable catheter-deployable soft-robotic sensor arrays for efficient left-atrial mapping.

Section C describes conformal, non-occluding sensor arrays for internal organ structure mapping, sensing, and ablation.

A. A Catheter Deployable Soft-Robotic Inflatable Basket for Enhanced Conformability to the Left Atrium of the Heart In various potential embodiments, a cardiac mapping and ablation catheter may comprise collections of active, hydraulically actuated, soft-robotic actuators integrated with arrays of flexible electronic sensors that can perform mapping and ablation of the entire atrium. This system, once actuated, forces the electrode array into contact with the atrial tissue without occluding blood flow. Because the actuators and electronics themselves are constructed from soft, compliant, biocompatible, polyurethanes, they will bend and stretch to adapt to the curvature and unique anatomy of the patient. This addresses the shortcoming of existing multi-electrode catheters and, because the actuators are hydraulically driven, exchange of cooling fluids can allow for both mapping and ablation.

The present disclosure relates to a design for a soft robotic basket catheter that can be deployed in the left atrium of the heart. The present disclosure explores two different designs and evaluates their conformability by deploying them in four 3D print models based on patient left atria. By utilizing 'mock' sensor arrays made from pH sensitive material, the conformability of the designs can be assessed in various sizes to understand their ability to conform and deform to complex atrial anatomy. The results show outstanding conformability with the optimal design showing ~80% sensor coverage all atria evaluated (only ~90% of sensors were in locations where contact was expected). Further, these balloons did not exhibit other shortcomings of basket catheters, namely the bunching of individual basket splines in certain region of the atria. All of these attributes make this type of soft robotic basket catheter an ideal platform for sensors arrays for simultaneous electrical mapping of the entire left atrium. This may be applied for unstable arrhythmias like Atrial Fibrillation which cannot be effectively mapped by more conventional single or several electrode mapping catheters. Accordingly, the present disclosure describes systems and methods for more effective and conformal left atrial mapping for patients with atrial fibrillation.

Embodiments of the systems and methods of the present disclosure can include a zero-volume actuator with ultrathin sensor arrays which can enable them to fit within small diameter catheters. The soft actuators can provide active force to push sensors into contact with tissue without potential damage to tissue. Overall actuator structure can provide for conformal support to force sensor arrays in contact with tissue without occluding blood flow to atrium. Different modes of creating the balloon/actuator can include thermoforming thin walled tubing, heat pressing laser cut layers of elastomer or multilayer balloons with cutouts. Different approaches for flexible sensors/interconnects can include thin wires running through the body of the actuators. The systems and methods of the present disclosure can include different sensing modalities. The systems and methods of the present disclosure can include embedded force sensors to detect which electrodes are in suitable tissue contact.

Initially, multiple layers of polyurethane are heat pressed into conformal contact. A laser cutter is used to cut the desired actuator geometry from the films with conditions optimized to simultaneously cut and weld layers. The resulting structures are watertight and can deform based upon the geometry of the actuator. In addition, by creating asymmetries in the number of polyurethane layers used on one side of the actuator or the other, out of plane bending can be achieved. Once actuated, the bending of individual beams should result in a hemispherical actuated geometry. By integrating two planar actuator arrays designed in this way, it is possible to achieve the type of hollow spherical design which can provide full atrial coverage without occluding blood flow. Serpentine interconnects and electrodes, fabricated on planar substrates and transferred to the soft actuators will be integrated first with the surface area of the actuators. The electronic layer will be bonded to the polyurethane using thin layers of stretchable (>100% strain to failure) UV curable polyurethane adhesive. Finally, the interconnects will be encapsulated in an additional layer of UV adhesive to ensure that the metal traces lies in the neutral mechanical plane where it will undergo minimal strain upon bending. The electrodes themselves will be exposed so they can contact tissue and will not benefit from neutral mechanical designs. If needed, they can be reinforced with a layer of stiffer material underneath them to ensure that even as the actuator bends and stretches, locally, the strain in the electrode is minimized.

This section of present technical solution presents the design, fabrication and test results for a basket catheter that utilizes soft robotic technology, which can conform to complex patient anatomy, according to various potential embodiments. Two designs of basket-shaped balloons in 3 sizes were fabricated based on a CO2 laser cutting method from thin (<50 μm) thermoplastic polyurethane (TPU). The balloons were deployed in four soft-material 3D printed left atria, whose geometries were based on volume rendered segmentation of cardiac computed tomography (CT) scans. The coverage and conformability to the realistic patient anatomies was tracked with the small patches of pH paper that would indicate, via a color change, contact with a basic solution that lined the 3D printed atriums. We were able to demonstrate the conformability of these inflatable basket catheters to be as high as (85%) for the optimized design. To visualize the balloon's performance, we showed micro-CT images of balloons deployed in 3D printed models. These images show the ability of the balloons to adapt to complex patient anatomy and did not exhibit any spline bunching or other deleterious mechanical behavior. This platform has the potential to be coupled with electrical sensors for simultaneous multi-sensor mapping of atrial fibrillation (AFib) and other cardiac arrhythmias.

Introduction—Atrial fibrillation (AFib) is the most common cardiac arrhythmia and is associated with significant morbidity and mortality. The irregular, rapid and ineffective atrial contraction results in the formation of blood clots within the left atrium, thereby leading to an increased risk of thrombo-embolic events; with cerebrovascular events being the most devastating occurrence. Additionally, ischemic stroke was found to be the first clinical manifestation of atrial fibrillation in 37% of individuals <75 years with no prior history of cardiovascular disease. Further, stroke patients with prior atrial fibrillation were found to have a higher 30-day mortality than those with new-onset atrial fibrillation. Additionally, AFib can result in distressing palpitations or precipitations of heart failure.

For individuals who are symptomatic or have recurrence of AFib, despite rate +/−rhythm control, catheter mapping and ablation is a therapeutic option in the decision pathway. In this procedure, a minimally invasive electrode is used to map aberrant electrical pathways and trigger points, while a second catheter is used to ablate tissue with RF energy, thereby disrupting the underlying mechanism of the aberrant electrical signal. Nevertheless, catheter-based ablation techniques present inherent limitations, primarily related to the length of the procedure (typically lasts 4-8 hours) with success rates of only ~60% during the first attempt. These prolonged procedures may lead to patient discomfort and also run the risk of major complications, such as atrioesophageal fistula and pulmonary vein stenosis. Additionally, signal mapping is done point by point, thereby making it difficult to map unstable arrhythmia, such as AFib. This limitation is critical since many of the features thought to be essential to understanding the underlying mechanism of AFib require robust spatiotemporally resolved mapping.

To address the aforementioned limitations, classes of multi-electrode mapping catheter are being developed, termed basket catheters. Such catheters position arrays of electrodes on baskets deployed in the left atrium that consist of multiple bent metallic beams. Baskets are fabricated from stiff materials and make contact with tissue through passive mechanical designs, and as a result, ~40% of sensors may not provide meaningful data. Furthermore, the individual splines that comprise the basket often end up bunching into particular regions within the atrium, resulting in large unmapped regions of the atrium.

To address these issues, this section of this technical solution describes a design for actively actuated baskets that can act as a platform for sensor arrays. This design is based on soft robotic technology, whereby fluidic actuators, fabricated from intrinsically soft materials are used to conform to complex and/or delicate anatomies. For the purposes of this disclosure, we discuss the design, fabrication and conformability of these baskets, however, the integration of sensors is beyond the scope of this work. These designs are pneumatically or hydraulically actuated, allowing them to more effectively conform against left atrial tissue. Furthermore, since these are actively actuated, the device can repeatedly conform and deform to ensure optimal contact with tissue. These designs can be fabricated from thin films of TPU, such that they can be used in percutaneous procedures. To characterize these designs, we deployed them in four soft 3D printed left atria, whose geometries were based on volume rendered segmentation of cardiac computed tomography (CT) scans. By using small patches of pH paper as mock sensors, we are able to show that optimized designs can show as high as 85% sensor coverage in different realistic patient anatomies. Furthermore, micro-CT imaging of balloons deployed in 3D printed models showed that they did not exhibit any spline bunching or other non-ideal mechanical behavior. Here, we describe the fabrication of these soft robotic platforms, several different designs, and their performance in cadaveric porcine and 3D printed human left atrial models.

Example Results and Discussion—We present the results for a catheter deployable basket-shaped soft robotic balloon, which can conform to complex patient anatomy as a potential platform for electrical sensors for mapping of atrial fibrillation (AFib) and other cardiac arrhythmias. The approach represents an unconventional use of elastomeric materials (i.e., TPU) for the structure of the basket catheter. Using layered sheets of TPU and a methodology for fabricating thin soft actuators, whereby a CO2 laser simultaneously cuts and welds the layered sheets (described elsewhere), we designed and fabricated a new generation of basket catheters which consist of a collection of active, hydraulically actuated, soft-robotic actuators. These balloons are thin enough to fit in the catheter as small as 8 Fr (2.6 mm, ID) and, once actuated, force themselves into contact with the atrial tissue without occluding blood flow due to its open-frame structure. Since the balloon is constructed from soft, compliant TPU, it will bend and stretch to adapt to the curvature and unique anatomy of the patient. Bending pneumatic/hydraulic actuators with individual slits have been studied in a previous work. The balloon patterns (star) reported here is inspired by this study where the individual segments allow for low pressure in this form factor actuator legs.

Figure 4:
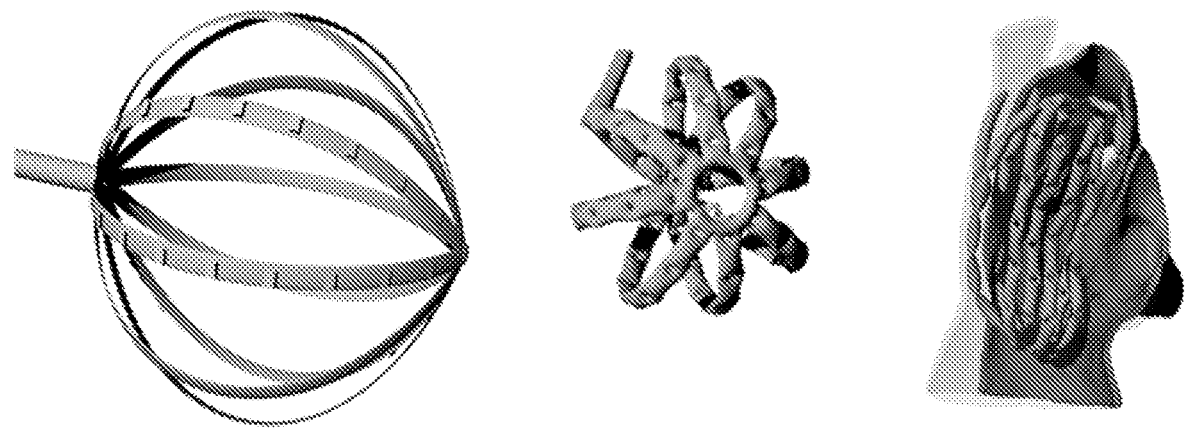
FIG. 4 depicts various example geometric configurations of balloon catheters with integrated sensors, in accordance with one or more potential implementations.

Referring now to FIG. 1 and FIG. 4, depicted is a schematic illustration of the fabricated balloon, with an array of sensors elements, along with various views of said balloon deployed in cadaveric porcine left atrium. While the actual fabrication of sensors is not addressed in this study, the ability of these sensors to conform to make contact with tissue is addressed. FIG. 1 shows the balloon deployed in a cadaveric porcine atria as viewed from outside and within the heart via an endoscope. Here, a small area of the atrial wall has been cut away to allow for visualization of the balloon. The individual actuators that comprise the balloon are all in direct contact with tissue. Furthermore, the individual beams of the balloon are evenly distributed radially within the atrium and do not show any signs of spline bunching, which is frequently observed in basket catheters. To further study the nature of the deployment of these balloons, they were inflated with contrast (5 vol % Omnipaque in DI water), deployed in 3D printed models, whose geometries were based off patient volume segmented CT images, and imaged via micro-CT (Siemens Inveon Multi-modality Scanner). The images of FIG. 1 provide an understanding of the configurations the balloons assume in order to conform to patient anatomies.

Figure 2:
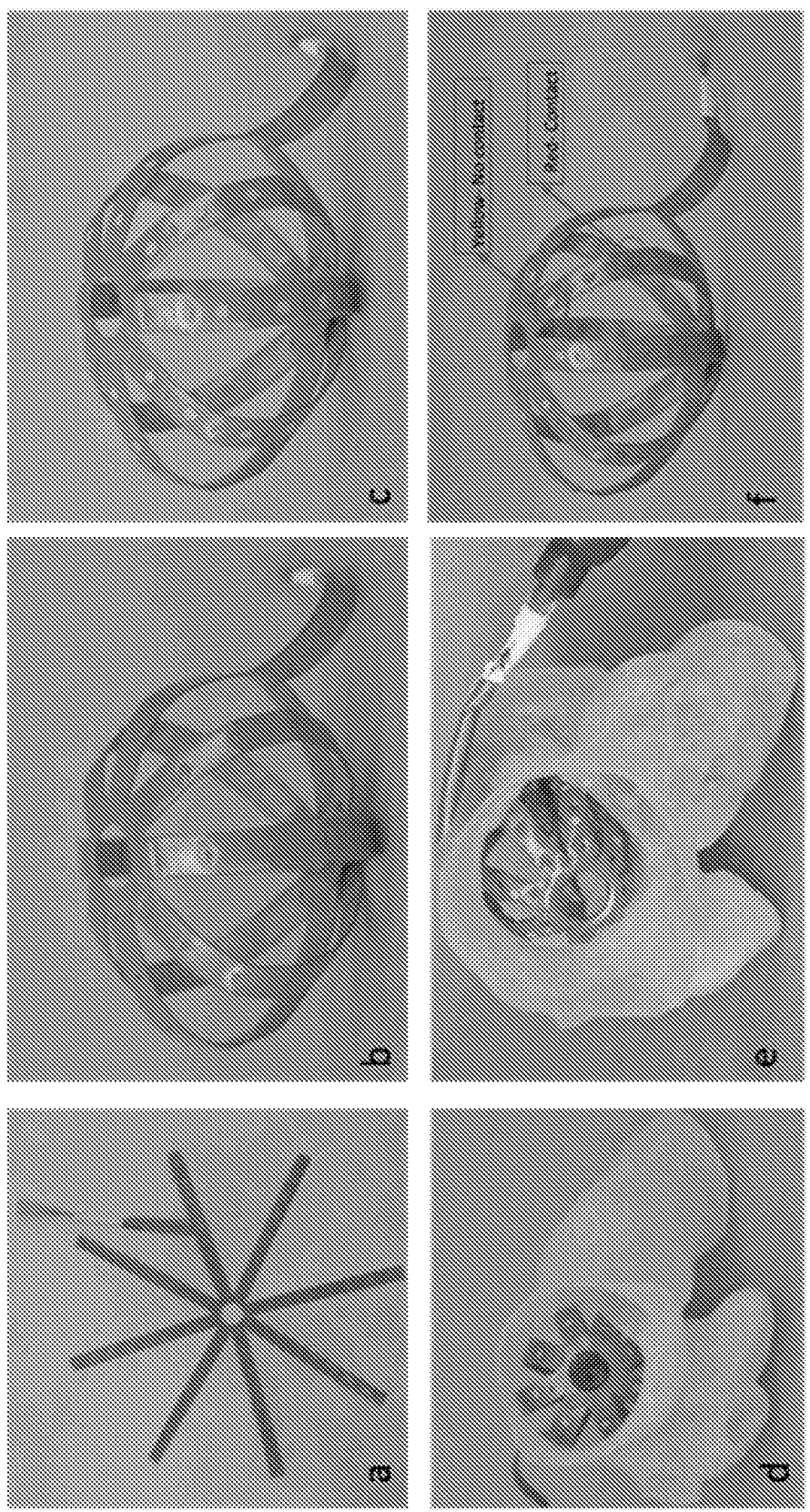
FIG. 2 depicts various views of an example balloon catheter with integrated sensors at different degrees of actuation, in accordance with one or more potential implementations.

The overall workflow for balloon fabrication as described herein consisted of heat pressing eight layers of TPU and laser welding them at their edge to form watertight interconnected channels within the single balloon. The resulting 2D balloons can be folded and assembled into 3D spherical structures as shown in FIG. 2. Each balloon consists of a basket of interconnected beams that are distributed evenly throughout the atrium without occluding blood flow. FIG. 2 illustrates the various steps in this workflow.

One critical aspect of the balloon performance is its ability to conform to the walls of the heart, allowing as many sensors as possible to be in contact. In order to optimize this aspect, we developed a test method to characterize the ability of balloons to conform to various cardiac anatomies. Here, balloons were covered in small 2 mm diameter dots of pH paper, meant to simulate an electronic sensor. Next, several left atrial models were 3D printed from soft materials (Tango plus-Stratasys) and coated with a thin layer of alkaline solution (Seventh generation dish liquid, pH=7-9). Balloons were deployed through the atrial septum (as in a mapping/ablation procedure) and inflated, allowing the mock sensors to be pushed into contact with the model. Typical EP systems can require at least ~0.6 seconds of physical contact to acquire meaningful data. Sensors in contact with the model were exposed to the solution and exhibited a color change, while actuators that did not contact the model remained unchanged, allowing for an assessment of the effectiveness of the balloons to conform within various patient anatomies. Significant care was taken to avoid the contact of these mock sensors to the edge of the model. In the present disclosure, two optimal designs in three different sizes are considered. The first design type, termed star-type, consists of eight independent beams. The second, termed sphere-type, possess a more continuous structure with segments interconnecting the individual beams. All of the balloons were tested inside 3D printed heart models for four random patients and the results are reported in this section. Each experiment was repeated three times and the standard deviation is reported in FIG. 7. FIG. 2 shows the fabrication and experimental steps.

Figure 3A:
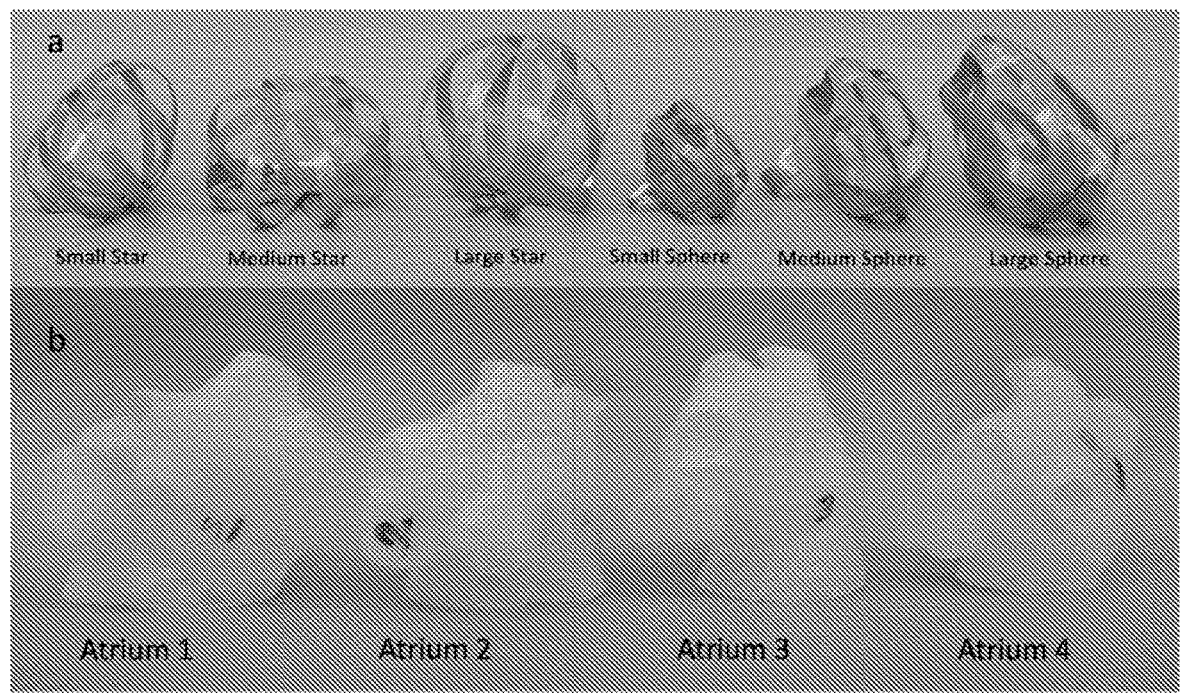
FIG. 3A depicts various example geometric configurations of balloon catheters with integrated sensors, in accordance with one or more potential implementations.
Figure 3B:
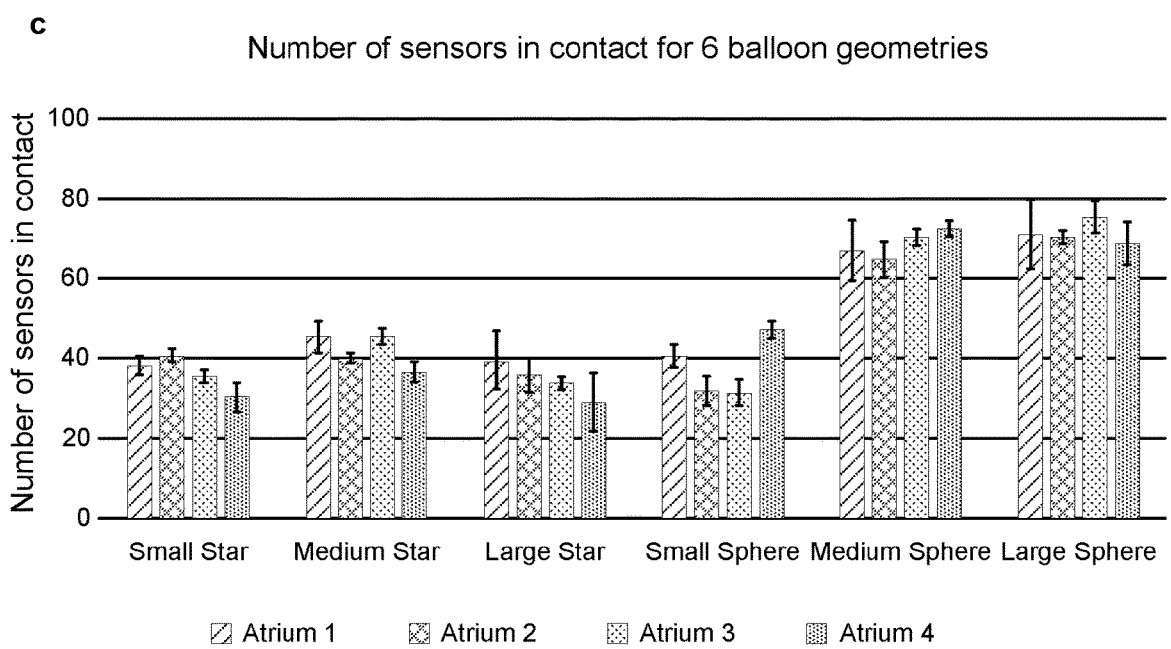
FIG. 3B depicts example experimental data relating to the number of sensors in contact with tissue for each of the example balloon geometries depicted in FIG. 3A, in accordance with one or more potential implementations.

The top row depicted in FIG. 3A shows the six balloon geometries evaluated and the four 3D printed atrial models used to assess their conformability. FIG. 3B shows the percentage and the number of sensors that were found to contact the various atrial models, respectively. Each bar shows the average percentage for three separate sets of experiments. It is noteworthy that a small number (~10%) of sensors lie in locations where they would not be expected to contact the model. The dotted line on FIG. 3B illustrates the maximum expected level of contact between the balloon and the 3D printed model.

Figure 8:
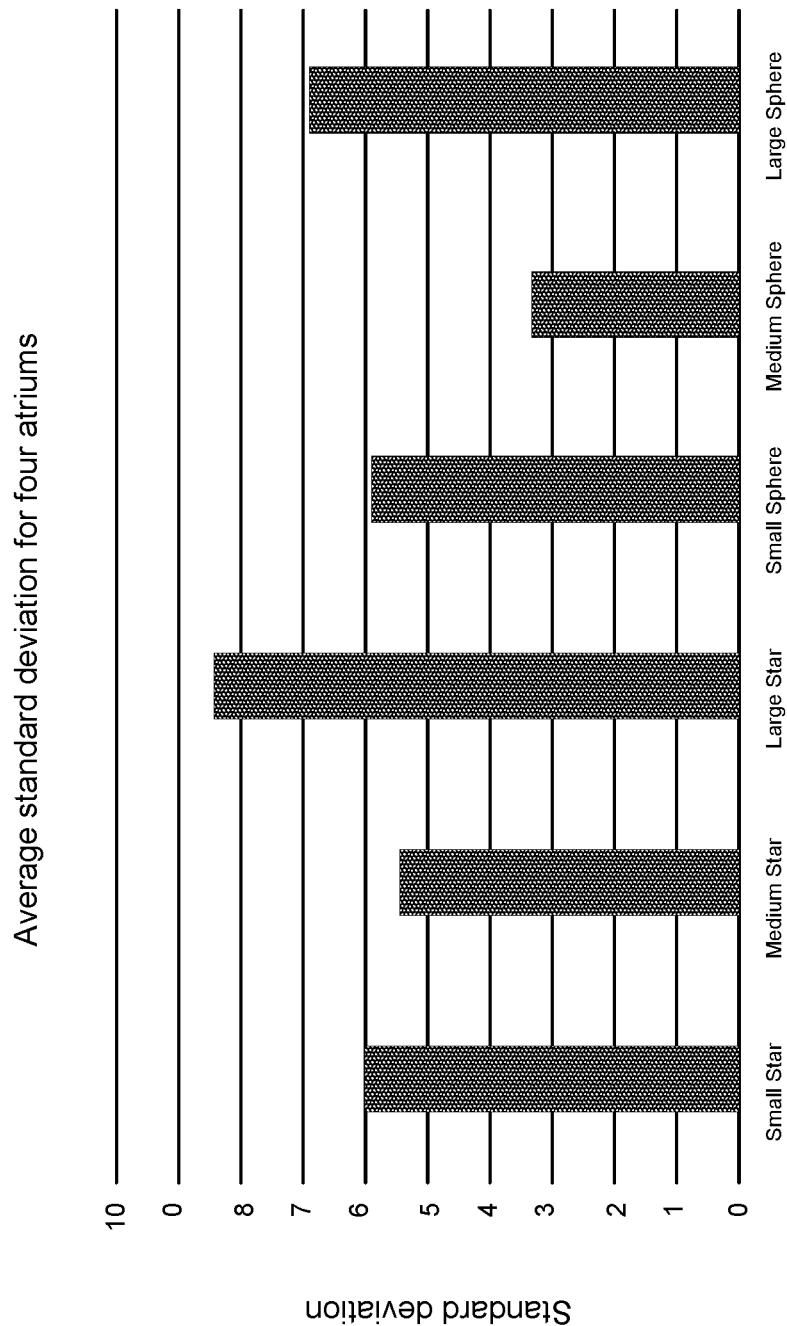
FIG. 8 depicts example experimental data relating to the average standard deviation of the example balloon geometries described herein, in accordance with one or more potential implementations.

In general, the models assessed showed effective performance with more than 50% of sensors in contact with the model in all experiments. However, the large sphere-type balloon showed the optimal performance with ~80% of sensors in contact for four atrial models tested. In general, less than optimal performance can be understood based on some combination of device under-sizing and, in the star-type balloons, actuator buckling. Since the buckling is stochastic, based on the detailed nature of contact between the balloon and the model, these designs also had a higher standard deviation (FIG. 8). Interestingly, the sphere designs appeared to be more insensitive to buckling, likely due to the links that connect the center of beams together and give more stability to the balloons. This corresponded to a lower standard deviation in these balloons. Overall, the sphere-type designs were more conformable and less sensitive to the sizing of the balloon relative to the patient atria. While there might be some applications where the star-type geometries are more desirable due to their simplicity or size, care should be taken that devices are appropriately sized.

FIG. 3B shows that the medium sphere-type and large sphere-type have the most number of sensors in contact with the atrial wall for all four 3D models (as high as ~75 in individual atria and ~70 average coverage across all atria). Furthermore, we conducted statistical analysis between these datasets (Table S2, shown herein below) to show the clear variation between proposed designs. It also appears from FIG. 9 that the highest percentage coverage is seen for medium and large sphere-types. Overall, these balloons have shown more consistent performance, higher average percentage and maximum number of sensors in contact with the atrium wall for all of the atriums. These two balloons are big enough to conform to the entire atrium and due to the robust structure of the sphere-type geometry, buckling is less likely to happen in this geometry.

In conclusion, this section of this technical solution describes a generation of the basket-catheter for the treatment of atrial fibrillation (AFib) and other cardiac arrhythmias. For this purpose, we utilized zero-thickness soft robotic technology and fabricated six different sizes and geometries of the non-occluding balloon. These balloons were fabricated by laser cutting thin layers of TPU in specific geometries, and then assembling them into hollow inflatable 3D spherical baskets. We characterized the conformability of these different geometries by covering the balloons with mock 'sensors' made from pH paper and assessed their ability to make contact with 3D printed atrial models, which were coated in alkaline solutions. This assessment was performed in four models, each fabricated from patient CTs. The results of the experiment showed two key outcomes. Unlike existing catheters, because the devices utilize flexible and conformal designs based on soft-robotics, they conform to the patient's unique anatomy and do not exhibit spline bunching. In all of the experiments, we have observed the conformability of 50%-85% for random patient's atrium models. The large sphere showed the best performance among all six balloons, with a maximum coverage of 85% and 75 sensors in contact with the atrium wall. This is likely attributable to the robust design which is highly interconnected to avoid buckling. This is a dramatic improvement over reported values for conventional basket catheters, where ~40% of sensors do not show actionable data. Furthermore none of the designs assessed showed spline bunching, as is commonly observed in basket catheters.

Finally, while these represent excellent platforms for integration of flexible sensor arrays, the conformability of the system can depend on the underlying mechanics of the sensor array and the method by which it is interfaced to the balloon. These highly conformable soft robotic systems represent a promising new approach to rapid mapping of the entire atrium which has the promise to dramatically improve the quality and understanding of AFib and other cardiac arrhythmia.

Example Experimental Data—Design and Fabrication of Non-occluding Balloons—In order to fabricate an ultrathin non-occluding balloon that conforms to the atrial wall, we utilized two 2D CAD designs, which upon assembly, can form 3D basket-shaped structures when attached in the manner presented in FIG. 2. Both designs yield a 3D basket-shaped sphere geometry which does not occlude blood flow and conforms to the atrial anatomy. Since, generally polyurethanes are biocompatible materials, to fabricate each balloon, soft polyurethane was used.

Eight layers of PU sheets were heat pressed (ACP composites) to each other (220 F, 600 sec). This process removed wrinkles or voids in or between PU layers without bonding the layers to each other. Then PU layers were simultaneously cut and welded into 2D patterns (based on AutoCAD designs) using a laser cutter (Universal Laser). For optimal performance, three consecutive cuts were performed with the same pattern, each with slightly varying conditions (500 PPI, Power: 80%, 85%, 90%, Speed: 40%, 35%, 30% respectively). Balloons were leak tested by applying pressure up to 10 PSI (nordson EFD) and then assembled into their 3D geometry by bonding the ends of the actuators at a point (using glue or tape). The resulting 3D balloon structure can be seen in the top row of FIG. 3A.

Figure 12:
FIG. 12 depicts an example table showing example dimensions of six example balloon geometries, in accordance with one or more potential implementations.

We designed two main 2D patterns, Star and Sphere, which can be seen in the top row of FIG. 3A. Both designs consist of interconnected beams of soft robotic actuators and once actuated, they will make hollow spherical balloons that provide for full coverage of the atrium without occluding blood flow. We fabricated 3 different sizes of each pattern with the exact same process. Table S1, illustrated in FIG. 12, shows the characteristics of each balloon.

Test the Conformability and Balloon Mechanics in Patient-Specific 3D Printed Models—This is sometimes referred to as the "pH method". In order to test the performance of the soft-robotic balloon, we created patient-specific 3D print models of the atrium from flexible materials (Tango plus-Stratasys). These 3D models are meant to recapitulate the mechanics of the atrium, based on volume segmented computed tomography (CT) images for 4 random patients. To create 3D models, first CT images were segmented (Mimics) and the blood volume of the left atrium was obtained using threshold filters. The segmented regions were exported as a 3D mesh (.STL file) which was then decimated, smoothed and cleaned (Geomagic) prior to printing (Stratasys OBJET260 Connex). To track the coverage area, we designed an experiment which uses pH sensitive paper to calculate the coverage area as well as the number of pH sensors in contact with the atrium wall.

The pH Experiment—pH sensitive papers (Educational Innovation Inc.) were cut into 2 mm dots using a biopsy punch (Integra Miltex, 2 mm). These served as mock sensors that were attached to the balloons with double sided adhesive 3M scotch tape. The sensors were placed in a uniform linear distribution on each balloon with a spacing about 10 mm such that the number of them is varied between 48-90 based on balloon area and geometry, as depicted in FIGS. 2 and 3A.

For each experiment, the inside of the 3D printed model was covered with an alkaline solution (Seventh generation dish liquid, pH=7-9) which results in a color change (yellow to red) in the pH paper that contacts it. The balloon was inserted into the left atrium and inflated with air (7-10 psi, Nordson). After 30-sec the balloon was deflated and removed from the model. Care was taken to ensure the deflated balloon did not inadvertently contact the model. Finally, the contact area and the number of sensors were measured. We repeated this experiment for each atrium and balloon geometry 3 times.

FIG. 1 and FIG. 4 depict schematic illustrations of the balloon devices described in this section. The remaining images depicted in FIG. 1 include images of the balloon devices described in this section deployed in cadaveric porcine left atrium. A portion of the left atrium has been removed for visualization. Images taken from inside the atrium were captured with an endoscope. The images of FIG. 1 designated e-f include micro-CT images and volume rendered segmentations of balloons deployed in left atrial models showing the conformability of the geometries.

FIG. 2 depicts various views and steps of a fabrication process for an example balloon device as described in this section. The top left photo of FIG. 2 depicts a 2D balloon fabricated by laser cutting method. The top-middle image of FIG. 2 depicts a 2D balloon folded and assembled into 3D geometry. The top-right image in FIG. 2 depicts a 3D balloon with pH sensors. The bottom-left image in FIG. 2 depicts a 3D balloon that is inserted in a 3D printed atrium model. The bottom-middle image in FIG. 2 depicts an inflated 3D balloon inside the atrium model. The bottom-right image in FIG. 2 depicts a 3D model after the experiment as described herein above. Sensors show the contact with the wall and yellow sensors show non-contact areas.

FIGS. 3A and 3B depict example images of various balloon configurations as described herein. The top image of FIG. 3A depicts six different balloons geometries described in this section. The bottom image of FIG. 3A depicts four patient specific left atrial models balloons that were tested and described herein. FIG. 3B shows example experimental data of the number of sensors in contact with each atrial model in the bottom image of FIG. 3A for the six balloons shown in the top image of FIG. 3A.

Soft robotic designs for basket catheters are developed and their conformability is assessed in patient specific 3D print models segmented from human cardiac CT images. The results show that designs showed improved conformability when compared to the reported performance for conventional basket catheters. Furthermore, the designs show more reliable mechanical actuation than typical basket catheters, where individual splines often bunch.

Validating the pH Method—In order to validate the pH method, 3D printed parts were fabricated with recessed grooves 0.5, 1 and 2 mm deep. These recessed structures were covered in pH paper and then placed in contact with a planar surface coated in alkaline solution. After 30 sec the structures were removed. The pH paper on the surface of the features made contact with the planar part and showed a color change (shown as different shades in FIG. 5), while the recessed regions did not show a color change. Thus, this method can be used to determine whether two surfaces have made contact with one another with at least 0.5 mm precision.

Figure 6:
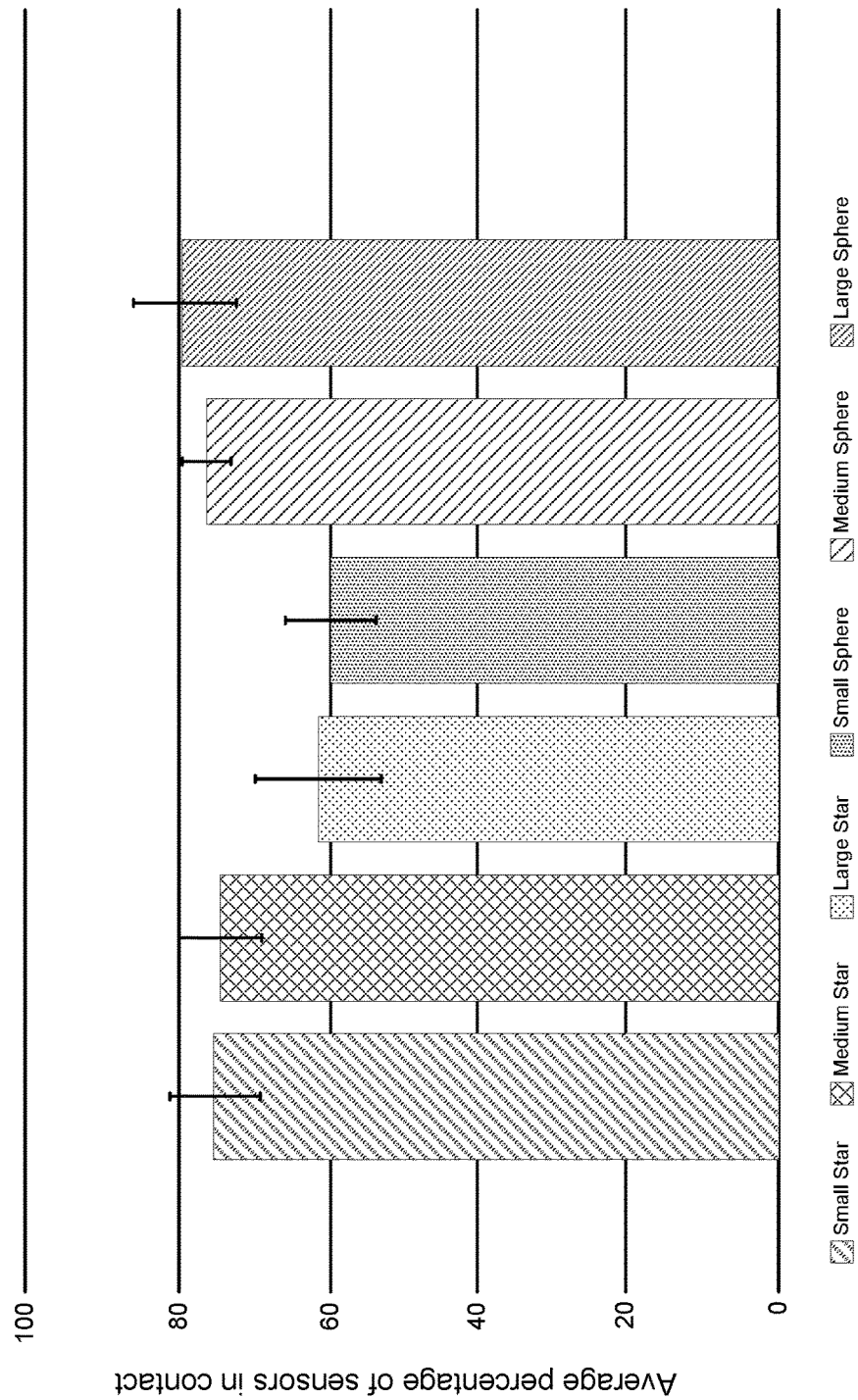
FIG. 6 depicts example experimental data relating to the average percentage of sensors in contact with an atrial model for example balloon geometries described herein, in accordance with one or more potential implementations.

Average Results for Six Balloons—FIG. 6 shows example experimental data of the average percentage of sensors in contact with the four atrial models (e.g. of the bottom image of FIG. 3A) for the six balloons shown in the top image of FIG. 3A. Based on this figure all of the experiments in average show 60%-80% of coverage and the large sphere configuration has the largest average coverage among all the balloons.

Figure 7:
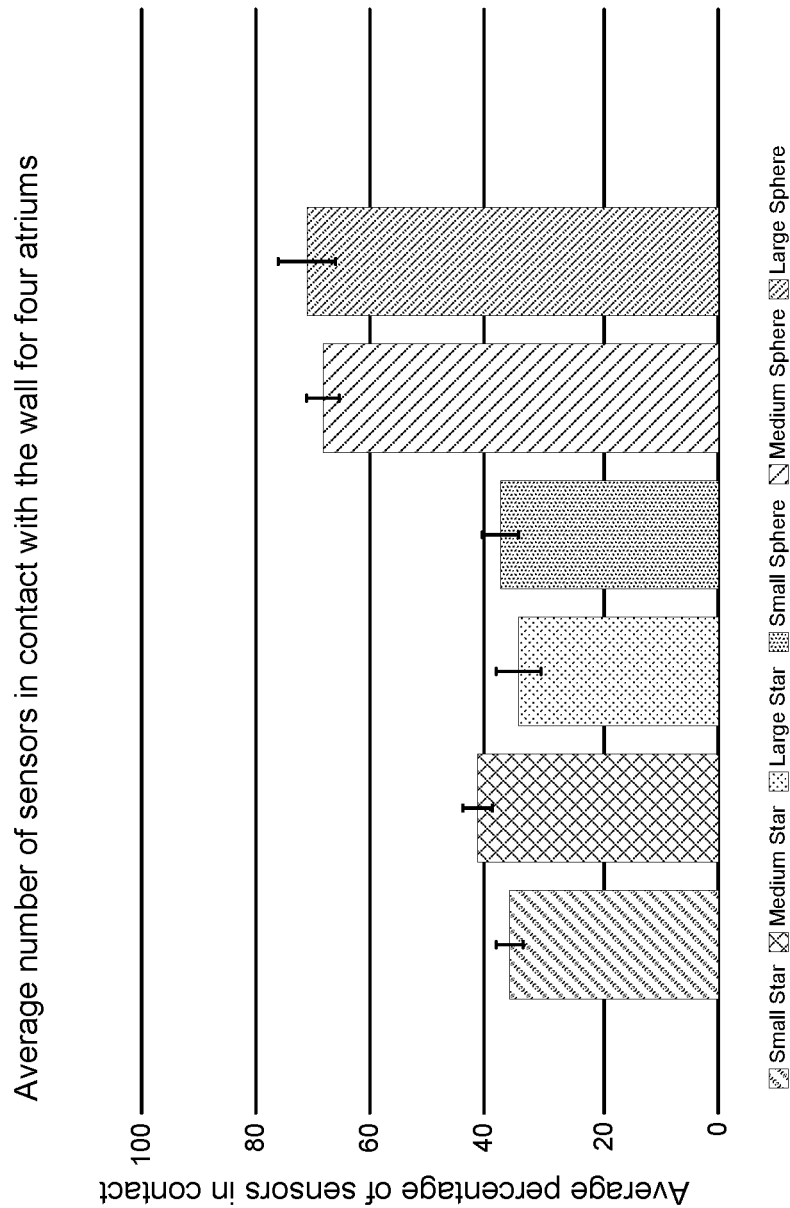
FIG. 7 depicts example experimental data relating to the average number of sensors in contact with an atrial model for example balloon geometries described herein, in accordance with one or more potential implementations.

FIG. 7 demonstrates the average number of sensors in contact with the four atrial models for the six balloons. Based on this figure all of the experiments in average show 36-71 sensors in contact with the atrial wall. The large sphere has the maximum average of the sensors (71) in contact with the atrial wall among all the balloons.

FIG. 8 shows the average standard deviation for the six balloons and four atrial. As shown in the figure, the large star has the maximum deviation due to buckling problems.

Sizing Analysis—The first design explored was the star pattern. This design was chosen to provide a similar structure to existing basket catheters with 8 splines evenly distributed to form a roughly spherical overall geometry. This design showed relative improvements that can be achieved by replacing basic passive actuators which engage tissue as mechanical buckling forces them to bend until the make contact with the sidewalls of the patient atria, with soft robotic bending actuators. These designs showed fairly effective performance with more than 50% of the sensors being in contact with the model in multiple experiments. While these results represent a general improvement when compared to prior reports of traditional basket catheters, these designs were still somewhat sensitive to the size of the patient atrium. Most notably, the individual splines would buckle slightly and lose contact with the tissue in some areas when the overall basket was too large for the atrium, which explains why the medium star design showed better performance than the large star design (the small star was undersized, making it difficult to make simultaneous contact with all areas of the atrium at once).

To reduce the amount of buckling, we explored a second design, termed the sphere design. Here, rather than interconnecting the balloon using linear splines, we created a curved interconnection pattern shown in FIG. 3a. This 2D pattern could be assembled into a 3D spherical geometry that is still open, allowing blood flow during deployment, however the degree of interconnection between inflatable features tended to prevent buckling in individual regions of the basket. It is for this reason that we saw good performance in both the medium and large configuration across all patient atria. These interconnected patterns provide more robust actuation that is less sensitive to buckling when oversized.

Figure 5:
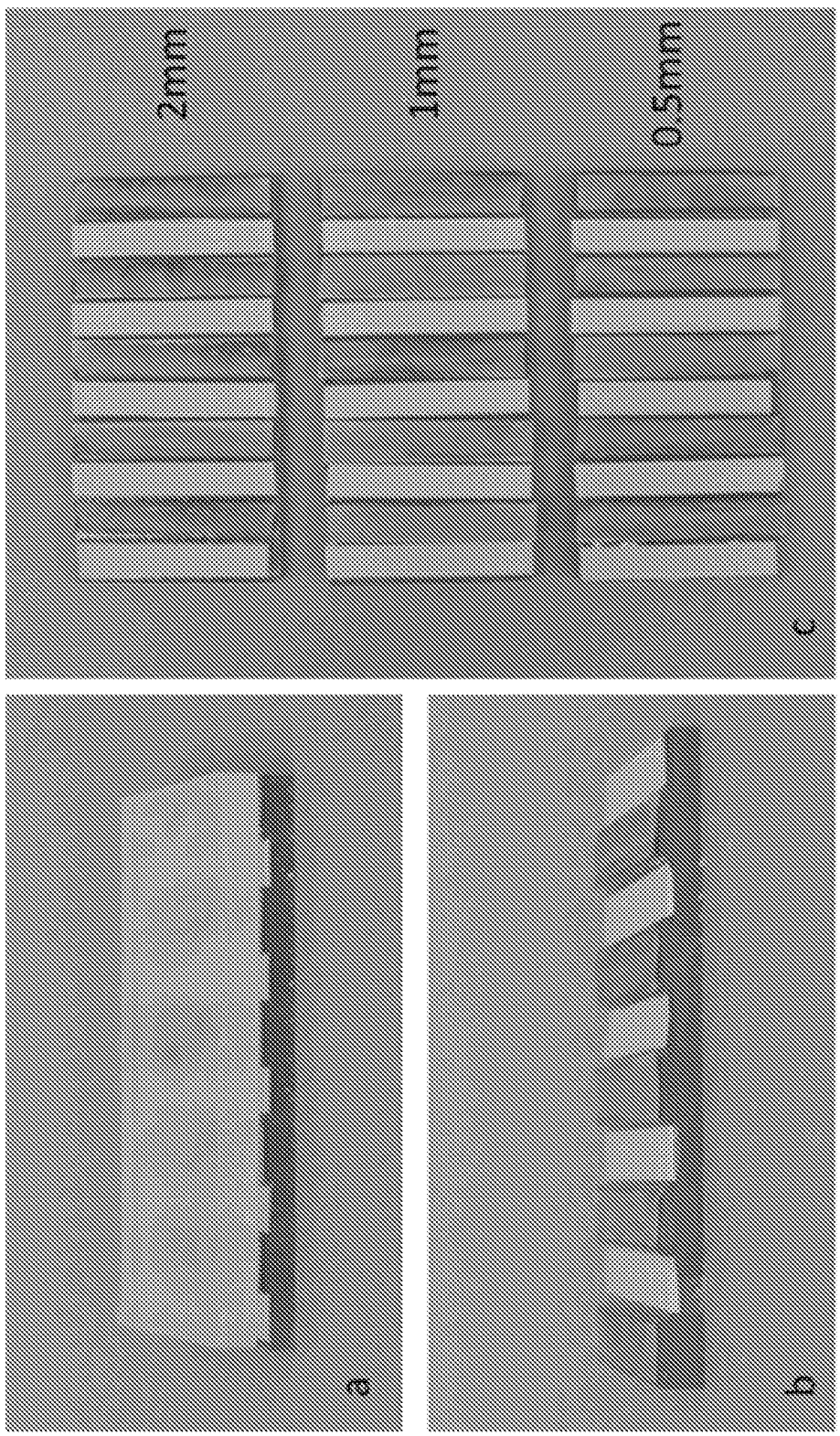
FIG. 5 depicts example pH validation steps of 3D recessed structures, in accordance with one or more potential implementations.

FIG. 5 shows the pH validation steps as described herein above. The top-left image of FIG. 5 shows 3D recessed structures covered with pH sensitive paper in contact with the planar surface covered with the soap. The bottom-left image of FIG. 5 shows color changes in the contact area. The rightmost image of FIG. 5 shows three sizes of the structure after the test.

Figure 9:
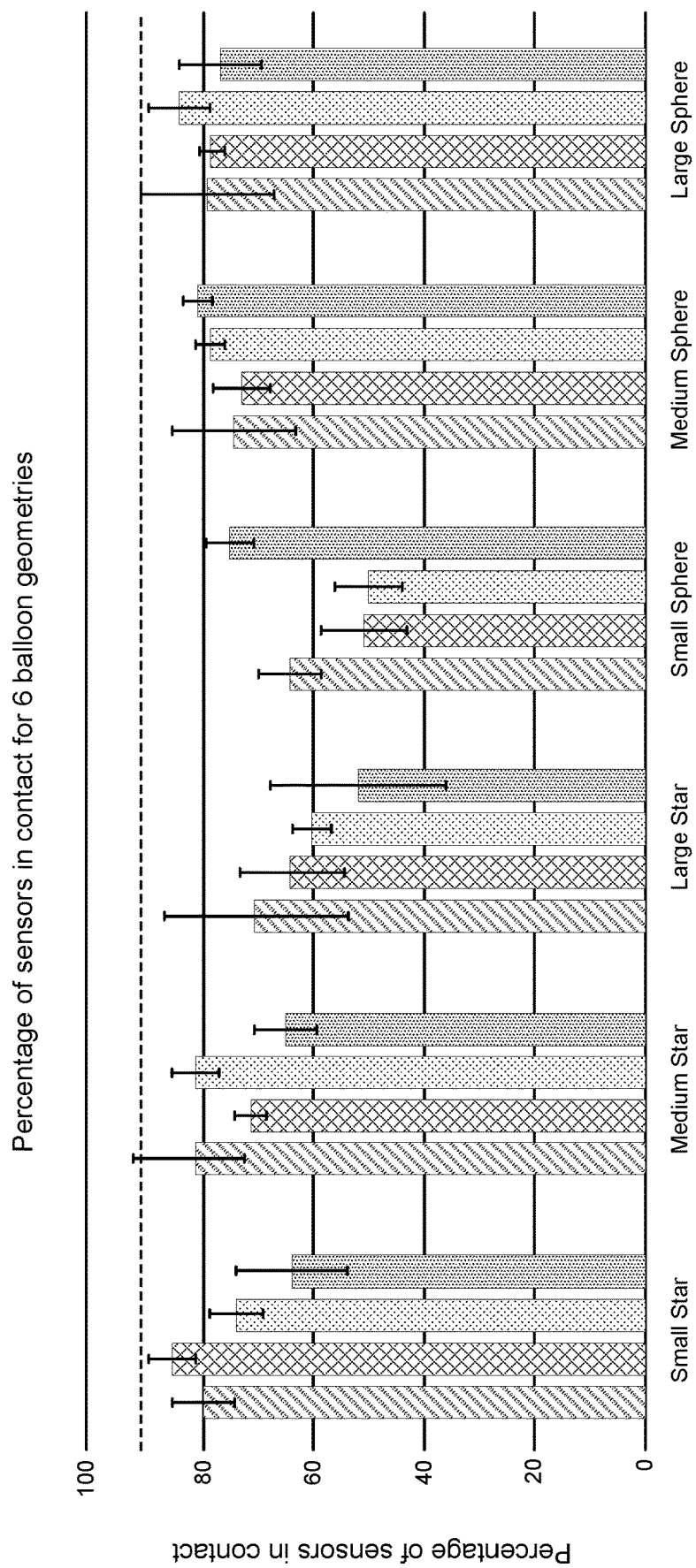
FIG. 9 depicts example experimental data relating to the percentage of sensors in contact with four different atrial models for six example balloon geometries as described herein, in accordance with one or more potential implementations.
Figure 10A:
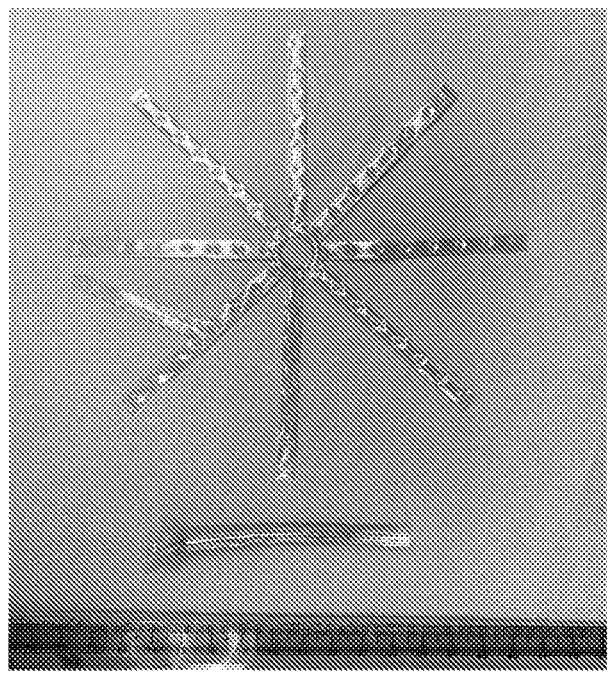
FIG. 10A depicts an example star balloon geometry with integrated sensors, in accordance with one or more potential implementations.
Figure 10B:
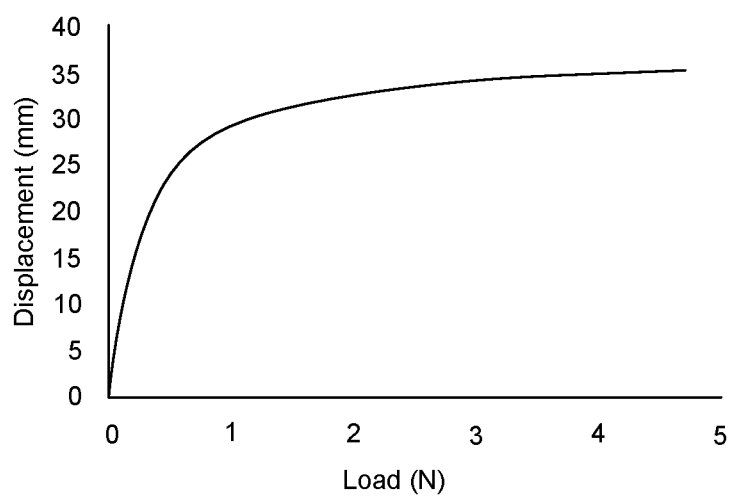
FIG. 10B depicts example experimental data showing a relationship between the displacement of the balloon in response to a compression force, in accordance with one or more potential implementations.
Figure 10C:
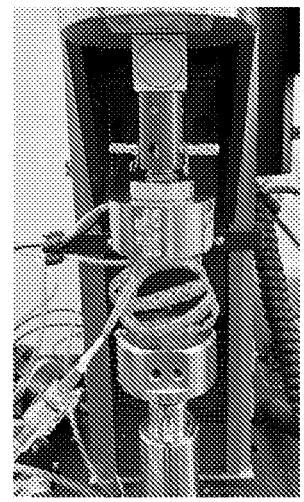
FIG. 10C depicts an example configuration of an experimental setup used to gather the data depicted in the graph of FIG. 10B, in accordance with one or more potential implementations.

FIG. 6 shows the average percentage of sensors in contact with atrial model for the six balloons shown in the top image of FIG. 3A. FIG. 7 shows the average number of sensors in contact with atrial model for the six balloons shown in the top image of FIG. 3A. FIG. 8 shows the average standard deviation for the six balloons and four atrial models shown in the bottom image of FIG. 3A. FIG. 9 shows the percentage of sensors in contact with atrial model for the six balloons shown in the top image of FIG. 3A. FIG. 10A shows the star pattern balloon pulled into a short mock catheter with an 8 Fr. diameter Compression Test—A tabletop universal testing machine, depicted in FIG. 10C, was used to perform compression mechanical testing on the inflated balloon. The balloon was inflated to a pressure of 10 PSI and placed between grips on either ends as shown in FIG. 10C. The pressure was monitored continuously using a pressure gauge. The load was increased gradually from 0 to ~5 N. As shown in FIG. 10A, for a small load of <1N, a large deformation takes place indicating easy conformability of the balloon. FIG. 10B shows an example graph of the displacement in the balloon subjected to loading. FIG. 10C shows a compression mechanical test conducted on a balloon inflated to 10 PSI pressure.

Flow Experiments—In order to illustrate that these balloons do not occlude blood flow when deployed in the left atrium, a flow experiment was conducted as described below. A flexible 3D print model was connected to a pulsatile flow pump to mimic realistic cardiac flows. The deployed balloon was observed using an endoscope. Videos of the flow experiments and FIGS. 11A and 11B show that the balloon could deploy effectively and that it did not occlude blood flow. FIG. 11A shows an example balloon deployed into the left atrium model and inflated, and FIG. 11B shows a flow experiment that was conducted using a pulsating flow pump. FIG. 11C includes an FE analysis for maximum deformation of balloon actuator with variation in thickness of polyimide.

Table S1 is depicted in FIG. 12 of the drawings.

TABLE S2

ANOVA analysis on number of sensors in contact (Posthoc by Turkey method)

| P values | Small star | Medium Star | Large Star | Small Sphere | Medium Sphere | Large Sphere |
|---|---|---|---|---|---|---|
| Small star | — | 0.44 | 0.99 | 1.00 | <0.01 | <0.01 |
| Medium Star | — | — | 0.82 | 0.58 | <0.01 | <0.01 |
| Large Star | — | — | — | 1.00 | <0.01 | <0.01 |
| Small Sphere | — | — | — | — | <0.01 | <0.01 |
| Medium Sphere | — | — | — | — | — | 0.85 |
| Large Sphere | — | — | — | — | — | — |

Figure 13:
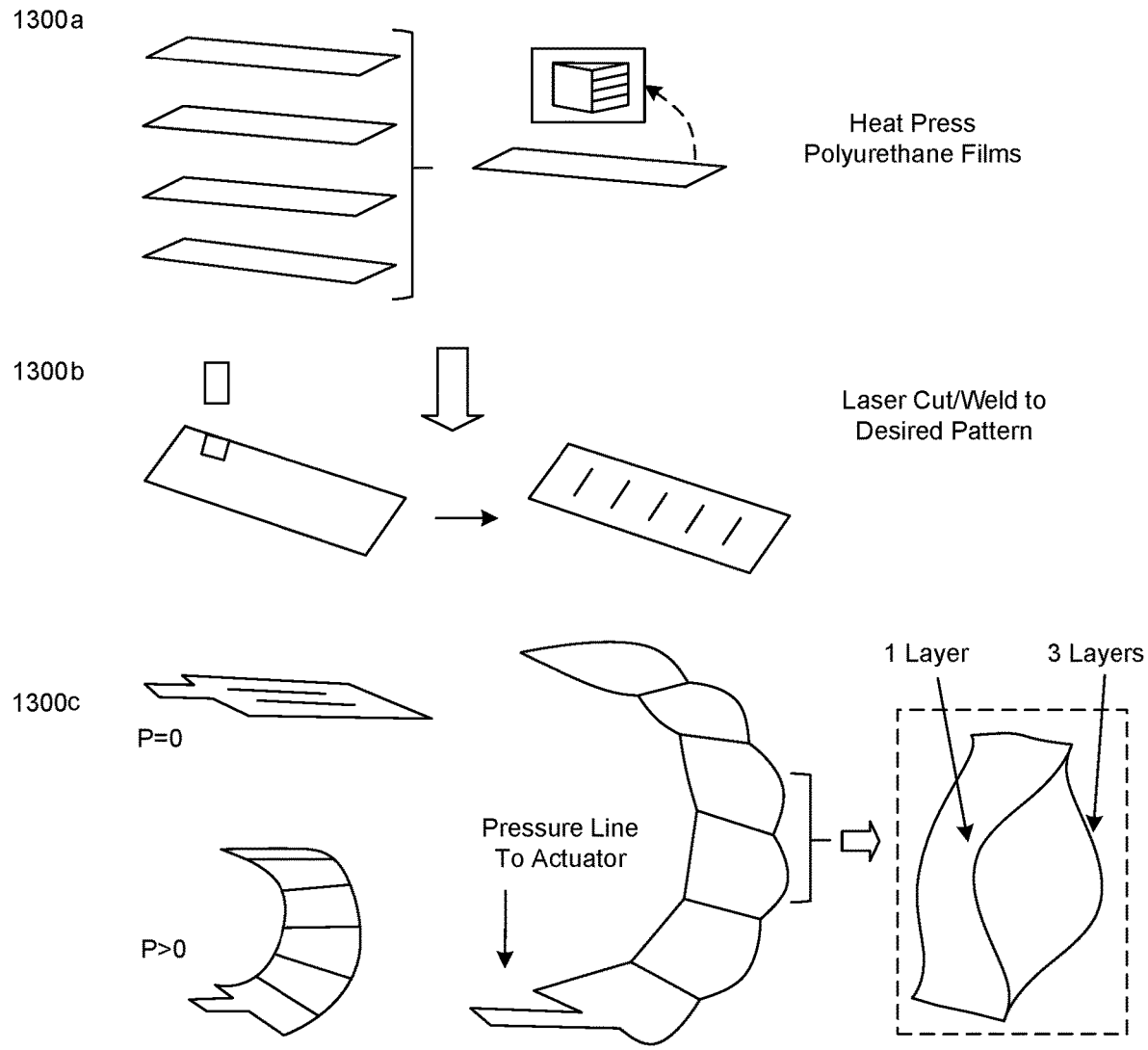
FIG. 13 depicts an example fabrication process for a portion of an example balloon as described herein, in accordance with one or more potential implementations.

Referring now to FIG. 13, depicted is an example fabrication process of an example balloon. At step 1300a, four layers of thermoplastic polyurethane are heat pressed to conformal contact. At step 1300b, a laser beam cuts the layers with a desired pattern. At step 1300c, the inflated chamber is bounded by 1 and 3 layers on its sides; the asymmetry of the stiffness leads to a bending motion.

Figure 14A:
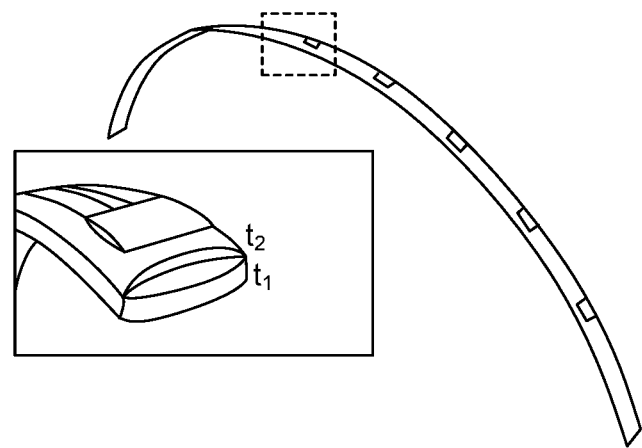
FIG. 14A depicts an example schematic illustration of an individual SRA beam with an integrated flexible electronic array, in accordance with one or more potential implementations.
Figure 14B:
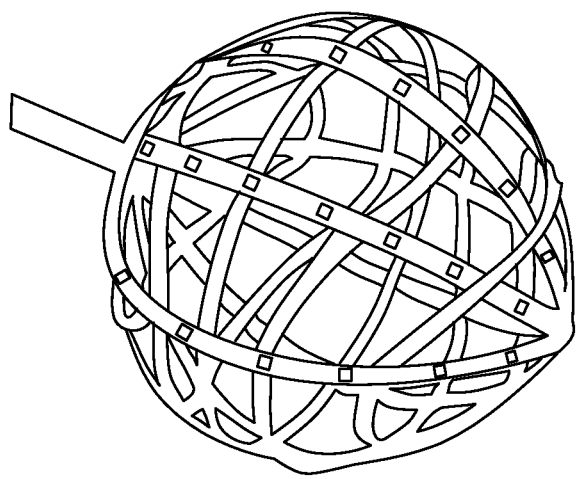
FIG. 14B depicts an example schematic illustration of a catheter deployed mapping and ablation balloon based on array actuators, in accordance with one or more potential implementations.

Referring now to FIG. 14A, depicted is a schematic illustration of an individual soft-robotic actuator beam with integrated flexible electronic array. Referring now to FIG. 14B, depicted is a catheter deployed mapping and ablation balloon based on array actuators.

Figure 15:
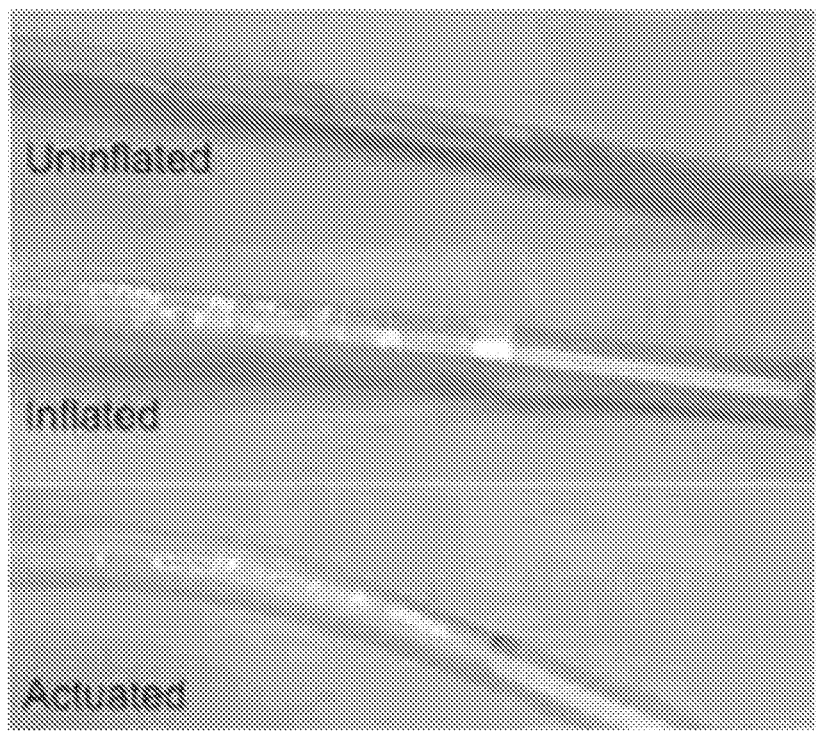
FIG. 15 depicts an example integrated SRA with flexible serpentine interconnects and temperature sensor, in accordance with one or more potential implementations.

Referring now to FIG. 15, depicted is an integrated soft-robotic actuator with flexible serpentine interconnects and temperature sensor. The device continues to function as the actuator bends. The top-most image of FIG. 15 depicts the soft-robotic actuator in an uninflated state. The middle image of FIG. 15 depicts the soft-robotic actuator in an inflated state, but not inflated to the point of actuation (e.g., where the soft-robotic actuator begins to bend according to its structural geometry). The bottom-most image of FIG. 15 depicts the integrated soft-robotic actuator in an actuated state, where the soft-robotic actuator is inflated to where the device begins to actuate, or bend, according to its structural geometry.

Although various implementations and geometries of actuator devices have been described in this section, it should be understood that any particular geometry of a flexible actuator can be used in the systems, devices, or methods as described herein. For example, certain actuator geometries may be suitable for certain inertial body structures, such as organs, veins, arteries, glands, tubes, cavities, or any other type of biological structure. As described herein and in the following sections, a variety of different sensing technology can be integrated with the soft-robotic actuators (SRAs) described in this section to accomplished a desired mapping, ablation, or sensing of biological attributes of a tissue, an organ, or a patient.

B. Multilayer Fabrication of Durable Catheter-Deployable Soft-Robotic Sensor Arrays for Efficient Left-Atrial Mapping Devices that perform cardiac mapping and ablation to treat atrial fibrillation provide an effective means of treatment. Current devices, however, have limitations that either require tedious point-by-point mapping of a cardiac chamber or have limited ability to conform to the complex anatomy of a patient's cardiac chamber. In this work, a detailed, scalable, and manufacturable technique is reported for fabrication of a multi-electrode, soft robotic sensor array. These devices exhibit high conformability (~85 to 90%) and are equipped with an array of stretchable electronic sensors for voltage mapping. The form factor of the device is intended to match that of the entire left atrium and has a hydraulically actuated soft robotic structure whose profile facilitates deployment from a 13.5-Fr catheter. Embodiments of the systems and methods described in this technical solution are suitable for conformable medical devices that leverage the characteristics of stretchable electronics and soft robotics.

Introduction—Atrial fibrillation (AFib) is the most common form of cardiac arrhythmia, with a worldwide prevalence of more than 33 million people worldwide. AFib causes an irregular and often rapid heart rate that may cause symptoms like palpitations, fatigue, and shortness of breath. It originates from the interplay between genetic predisposition, ectopic electrical activity, and abnormal atrial tissue substrate. AFib can affect the efficiency of cardiac output and promote the formation of blood clots inside the left atrium (particularly the left atrial appendage). If these clots embolize and travel from the heart to the brain, they could result in a stroke; AFib is associated with a 1.5- to 2-fold increase in death and heart failure and about 3- to 5-fold higher risk of stroke. Furthermore, AFib is also associated with a greater risk of hospitalization, with 10 to 40% of patients with this disease hospitalized annually.

Radiofrequency catheter ablation has emerged as an established and widespread technique for the treatment of AFib via a minimally invasive catheter procedure. Cardiac electrograms are mapped using a sensing catheter, and then radiofrequency energy is applied to the heart muscle at particular locations to cauterize the circuits that trigger AFib, using an ablation catheter. This procedure can provide rhythm control in patients with paroxysmal and persistent AFib. There is strong evidence that AFib ablation therapy improves quality of life, reduces health resource utilization, and improves heart function in patients with heart failure. For the ablation procedure, electro-anatomical mapping techniques have been developed to guide the procedure. By recording the electrical activity inside the heart, the circuits that are generating AFib can be identified. However, some electro-anatomical mapping systems have limited spatiotemporal resolution for detecting localized AFib drivers because of their sequential spatiotemporal characteristics, intermittent firing, and complex atrial anatomy. These are some of the reasons for suboptimal outcomes after ablation in some forms of AFib. Subsequently, advanced mapping catheters such as basket catheters with multi-electrode arrays mitigate this drawback. The advantages of multi-electrode mapping include quicker voltage mapping and more accurate assessment of activation sequence. However, conventional multi-electrode catheter designs are fabricated from sensor arrays that are deployed on a cage of inelastic materials (either metal wire or narrow strips of inelastic polymer film) designed to passively engage with tissue. These designs have limited conformability and other non-ideal mechanical response, such as spline bunching (i.e., a non-uniform distribution of the sensor arrays due to improper deployment/expansion of the device in the left atrium). The effective result of these unintended mechanical responses is that less than 50% of the sensors provide meaningful data. Here, we report the development of a soft robotic sensor array (SRSA) that uniformly conforms 128 flexible sensors to the left atrial tissue by hydraulically actuating a thin-walled polymer cage. We deployed these devices in four soft three-dimensional printed atrial models and found that an average of ~85 to 90% of the sensors expected to make tissue contact establish robust near-field sensing [<2 mm distance, as assessed by micro-computed tomography (μ-CT)]. Further, we were able to show the robustness of our designs by deploying them from a 13.5-Fr catheter tube and showing that sensors could undergo 100 cycles of actuation without reduction of performance.

Overall, development of these devices posed several challenges, namely, scalable fabrication, integration, and associated mechanical durability. To achieve conformable SRSAs, we used approaches for fabricating soft actuator designs with high degrees of complexity. We focused on designs that have been established for their ability to conform to patient atria. Here, we have developed an approach for post-processing flex-PCB with serpentine sensor array designs and integrating them with these approaches for soft actuator fabrication that can yield complex geometry SRSAs with 128 sensors. We describe a self-aligned post-processing method to remove inelastic flex-PCB substrates, providing them markedly increased flexibility, required for integration with soft actuators. These methods allow these devices to be fabricated without costly and time-consuming clean-room fabrication, using scalable flex-PCB manufacturing. The principles, procedures, and techniques discussed herein are valuable tools not only for this application but also for a wide variety of applications, where sensor arrays are integrated with soft actuators, especially when thin or low-profile designs are needed.

Results and Discussion—Starting from factory-manufactured flex PCB sensor array and thermoplastic polyurethane (TPU) sheets, a final cage device (i.e., SRSAs) is manufactured, which has high conformability in the left atrium. FIGS. 16-18E illustrates the key features of the SRSA design and its application for atrial mapping. Note that both transparent and colored TPU films can be used to fabricate these SRSAs. A laser-cutting post-processing step is introduced in this study to convert the flex PCB sensor arrays to stretchable sensor arrays as discussed in a later part of this study. Soft robotic actuators are fabricated from the TPU sheets using a combination of laser-cutting and heat-pressing steps. The stretchable sensor arrays are integrated with the soft robotic actuators to fabricate a single linear SRSA. Using a method for fabricating actuators with complex 2D geometry based on laser cutting, a complete fabricated SRSA cage was made with eight coupled linear actuators, each with 16 sensors. In the figure, SRSAs fabricated from transparent TPU allow for better visualization of the integrated flexible sensor arrays. Individual serpentine traces are visible in the inset. For typical atrial mapping procedures, an electrophysiologist would deploy the SRSA cage from a catheter through the puncture made in the foramen ovale in the patient's septal wall, which is the heart tissue that separates the right and left atrium. Here, devices were deployed in soft 3D printed atria based on real patient CT images to assess the conformability of the device. Soft tissue-like materials (TangoPlus) were used in the 3D printed models to mimic the mechanical properties of the atrial tissue. This is explained further in Materials and Methods.

The SRSAs were fabricated using a method that allows for creation of actuators with arbitrary 2D complexity, based on laser cutting and subsequent heat-pressed assembly of TPU and sacrificial PVA films, described elsewhere. We coupled this with 3D assembly of various 2D actuator patterns to yield the 3D soft actuator cage used in our design. In short, 2D actuators are formed by laser-cutting 2D patterns of water-soluble PVA and using it as a sacrificial layer to form closed channels between two bonded layers of TPU. While this process allows actuator geometries with significant complexity, it has the benefit that because it consists of an assembly of 2D planar actuator designs, these designs are intrinsically compatible with most scalable manufacturing methods for electronics. This is in contrast to many alternative methods to fabricate soft robotic actuators that require complex embedded 3D channels to allow for integration of sensors or electronics. In addition, most other actuators are intrinsically high strain (~100 to 400%) to yield actuation, and thus, they rely on materials with greater intrinsic stretchability than conventional flex PCBs.

Post-Processing of Stretchable Electronics—To provide electronics with the flexibility required for the integration with our soft actuators, we developed a versatile laser-cutting post-processing method to convert inelastic flex-PCB substrates into stretchable sensors. This technique presents several notable benefits: (i) Fabrication of stretchable sensor arrays can be done using flex PCB as a scalable starting component. (ii) The process is self-aligned, thus preserving the substrate polyimide (PI) material only under the individual traces, thus allowing for greater durability and robust-ness than isolated metal traces alone. (iii) Unlike alternative methods that remove the substrate entirely (e.g., etching), this technique can arbitrarily pattern stretchable regions, while other regions can remain stiff. (iv) The resolution of laser post-processing can be in the order of 10 μm. (v) The use of electronic sensor arrays without laser post-processing results in significant reduction in conformability.

Figure 19:
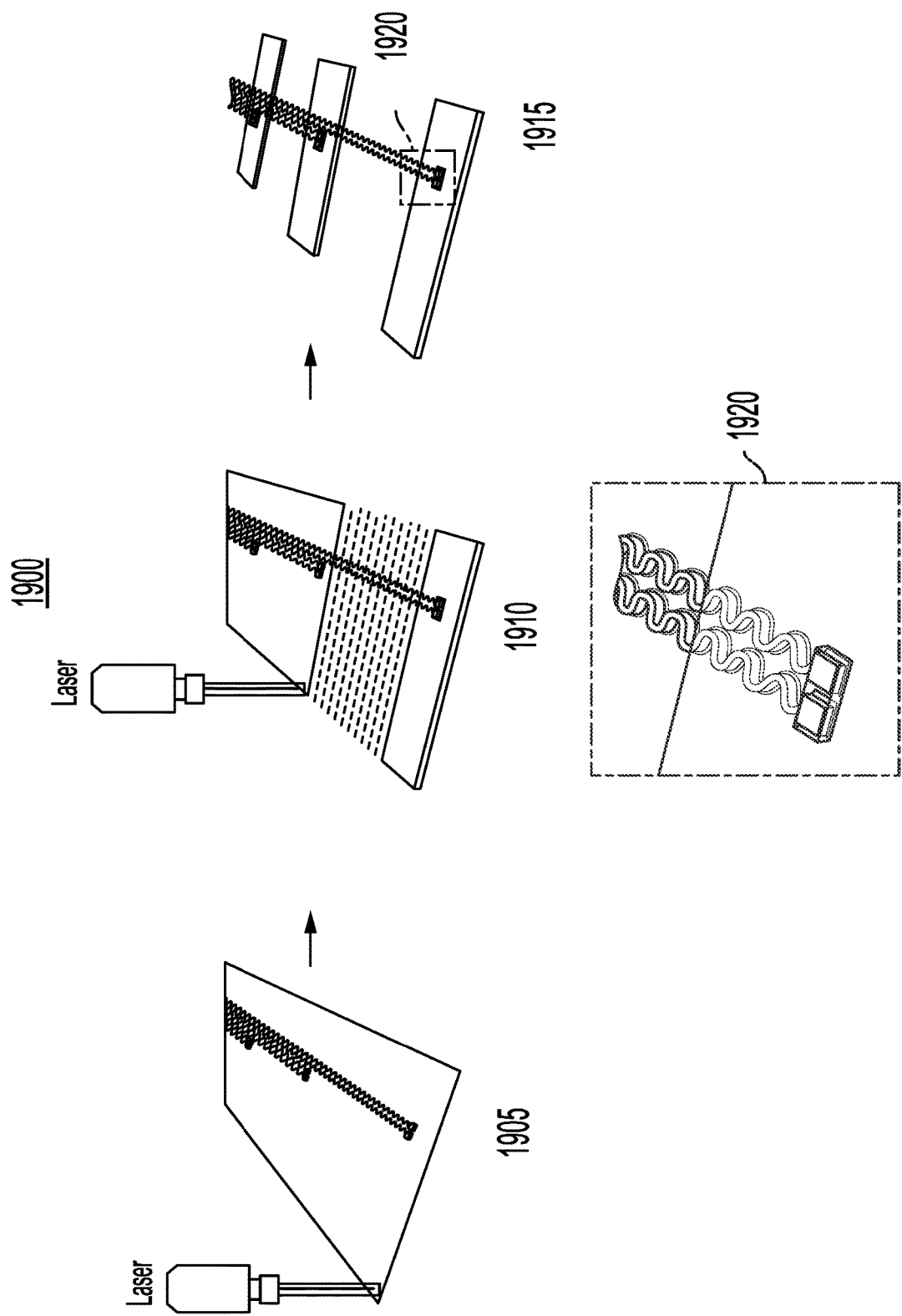
FIG. 19 depicts an example manufacturing process for stretchable electronics, in accordance with one or more potential implementations.

Referring now to FIG. 19, depicted is an example process of post-processing flexible electronic devices, as described herein. The design consists of three layers (Step 1905 in FIG. 19), namely, a copper layer sandwiched between two PI layers. The copper layer consists of serpentine traces connected to 16 electrodes on each flexible circuit board. Windows are provided on the top PI layer to expose the electrodes for contact. The thickness of the PI layer is ~20 μm and that of the copper layer is 15 μm. Therefore, the flex PCB initially has a uniform thickness between ~40 and ~50 μm. The extent to which the flex PCB can be actuated in the inflatable frame is a direct function of its thickness. Therefore, to ensure better actuation and subsequently better conformability of these electronics within the left atrium, a post-processing step was incorporated within the workflow. A $CO_2$ laser (Universal Laser, power 23%, speed 50%) was used to selectively remove the PI from sections of the flex PCB as shown in Step 1910 of FIG. 19. The laser rasters as indicated by dashed lines in the figure, thereby removing the excess PI. Note that laser conditions were optimized such that the PI is preserved underneath the traces. We believe that this is likely due to thermal masking, whereby the copper traces allow for heat to be rapidly spread, reducing peak temperatures and preventing the underlying PI from reaching temperatures sufficient for removal. Meanwhile, regions of PI not in contact with thermally conductive copper reached higher peak temperatures and were subsequently removed. We enhanced the stability of the entire array and prevented traces from losing alignment to one another by preserving the PI substrate as thin strips that connect neighboring traces (shown in step 1915 of FIG. 19). A close-portion of the thin strip of PI substrate is shown in view 1920 of FIG. 19. In addition, the insulation in the topcoat PI could be used for electrical isolation in regions where it is preserved.

Figure 20:
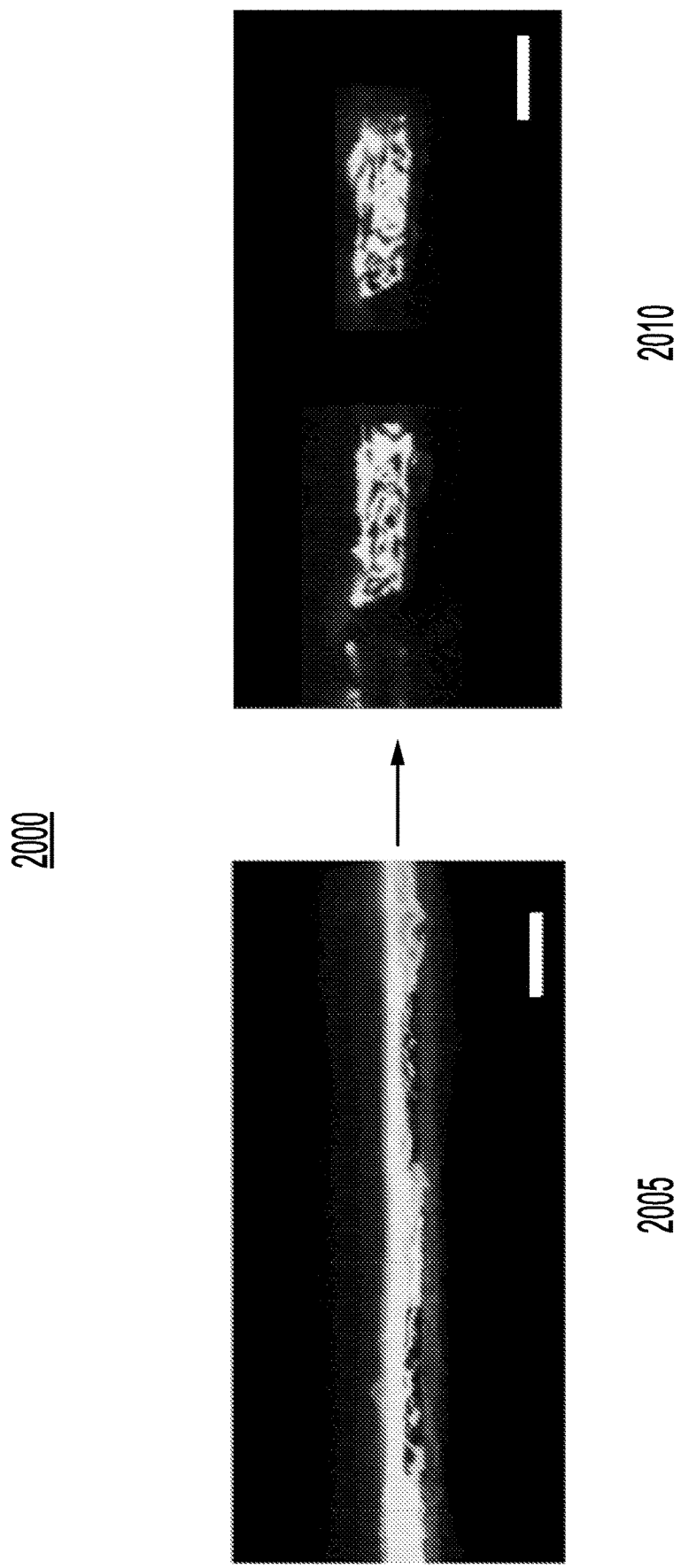
FIG. 20 depicts a cross-sectional confocal image of the electronics of FIG. 19 before laser cutting, in accordance with one or more potential implementations.
Figure 21B:
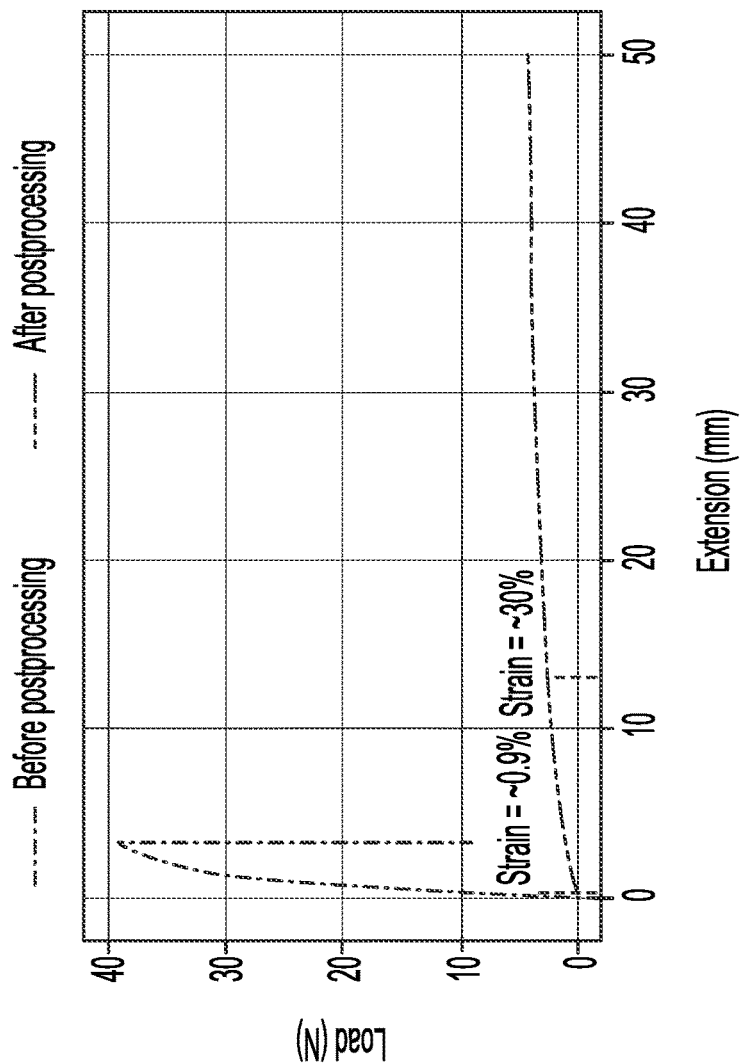
FIG. 21B depicts example experimental results for a tensile test for preprocessed and post-processed sensor arrays, in accordance with one or more potential implementations.
Figure 21A:
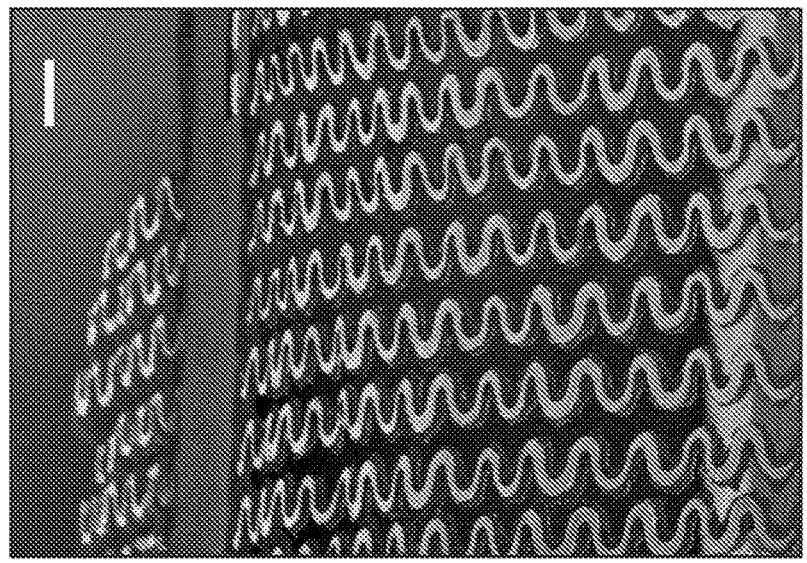
FIG. 21A depicts an example rendering image of a laser-cut stretchable electronics, in accordance with one or more potential implementations.

Referring briefly now to FIG. 20, depicted are cross-sectional (end-on) confocal images of the flex PCB that were taken before (2005) and after (2010) the laser-cutting process. The copper layer (black) can be seen sandwiched between two PI layers (fluorescent green) in image 2005 of FIG. 20. However, only one layer of bottom PI can be seen after the laser-cutting process in image 2010 of FIG. 20. Referring briefly now to FIG. 21A depicted is an SEM image of the flex PCB after the post-processing described herein.

To test the stretchability of an SRSA, a tensile test was conducted on a flex PCB and a post-processed array, both of which were sandwiched between two thermally bonded layers of TPU. Example experimental results from the tensile test are shown in FIG. 21B. A marked increase in strain can be observed from ~0.9% before post-processing to ~30% after post-processing at the breaking point of the serpentines, thereby showing excellent stretchability of the SRSAs. Note that preprocessed flex-PCB alone is incompatible with the soft actuators used for this design, as it is too stiff and inelastic to allow for actuation. Therefore, this post-processing step is critical for the success of the overall fabrication method.

Referring briefly now to FIGS. 16 through 18E, the flex PCB and TPU sheets are processed through various fabrication techniques to obtain a single linear SRSA from which an SRSA cage device is fabricated. This device is inserted into the left atrium using a mock catheter through the puncture made in the foramen ovale in the patient's septal wall.

Referring briefly now to FIG. 19, depicted is a process for post-processing of stretchable electronics. At step 1905, stretchable electronics are depicted prior to laser cutting. At step 1910, the selective laser-cutting process removes portions of the substrate. The rastering path of the laser is depicted as dotted lines in this step. At step 1915, the stretchable electronics are shown after post-processing. Inset shows the underlying PI preserved after the laser-cutting process. A close up portion 1920 is shown resulting from the step 1915. Referring briefly now to FIG. 20, depicted at image 2005 is a cross-sectional (end-on) confocal image of the electronics before laser cutting. Scale bar, 0.1 mm. Still referring to FIG. 20 and at image 2010, depicted is a cross-sectional (end-on) confocal image of the electronics after laser cutting. Scale bar, 0.1 mm. Referring briefly now to FIG. 21A, depicted is a SEM image of the final laser-cut stretchable electronics. Scale bar, 0.3 mm. In FIG. 21B, the results for the tensile test are shown between preprocessed and post-processed sensor arrays. The stretchability of the post-processed sensor arrays can be clearly observed.

Figure 22A:
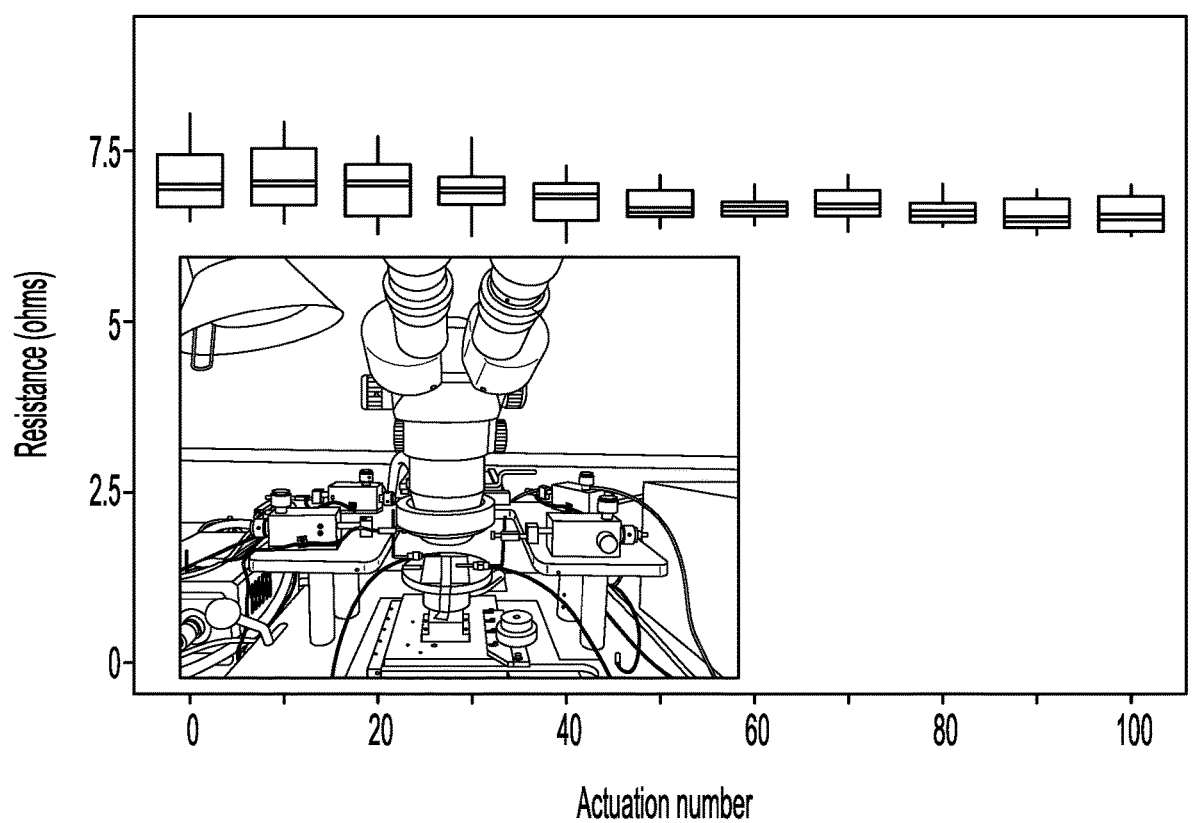
FIG. 22A depicts a plot of resistance as a function of actuations for a single actuator, in accordance with one or more potential implementations.
Figure 22B:
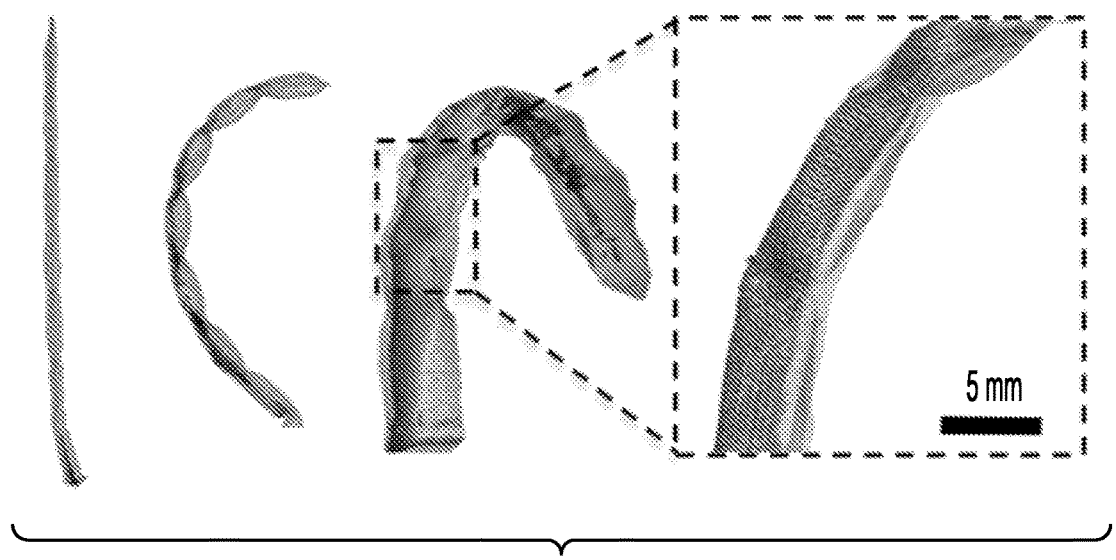
FIG. 22B depicts micro-CT images and volume-rendered segmentations of actuate linear soft-robotic sensor arrays, in accordance with one or more potential implementations.
Figure 23C:
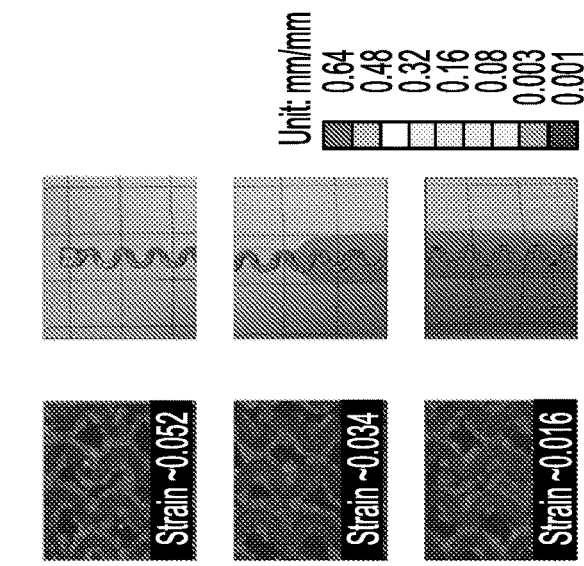
FIG. 23C depicts the three strain values selected in FIG. 23B compared between confocal images for an actuated pocket, in accordance with one or more potential implementations.
Figure 23B:
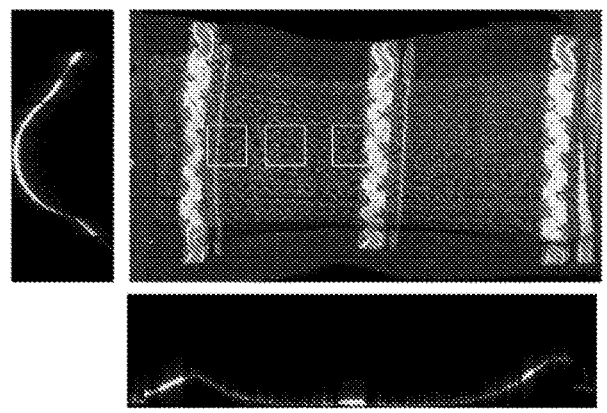
FIG. 23B depicts three locations where strain computations are extracted and compared between confocal images for an actuated pocket, in accordance with one or more potential implementations.
Figure 23A:
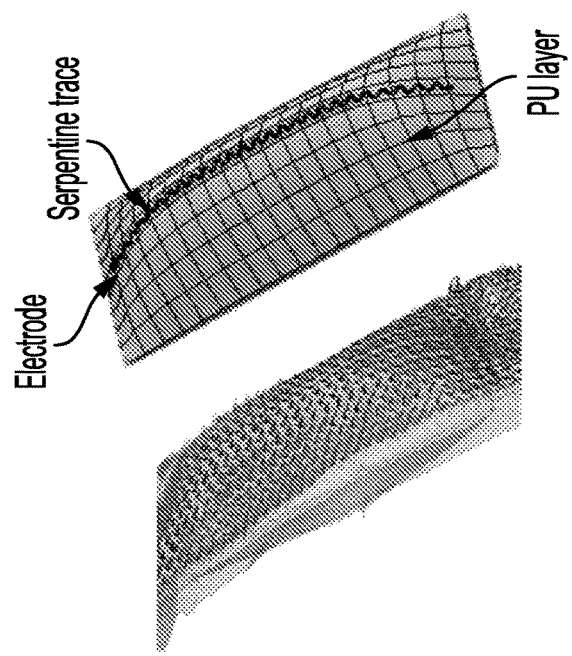
FIG. 23A depicts views of an example actuation pocket where maximum deformation takes place in a simulation, in accordance with one or more potential implementations.
Figure 25A:
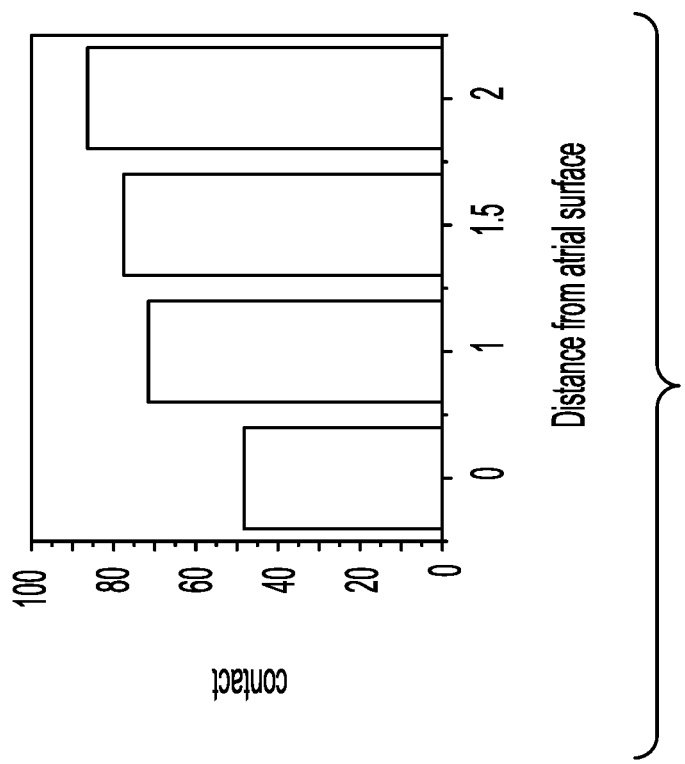
FIGS. 25A and 25B depict example experimental data showing the percentage of the sensors of the soft-robotic sensor arrays shown in FIGS. 24A and 24B respectively when compared to the distance of the sensor arrays from the atrial surface, in accordance with one or more potential implementations.
Figure 25B:
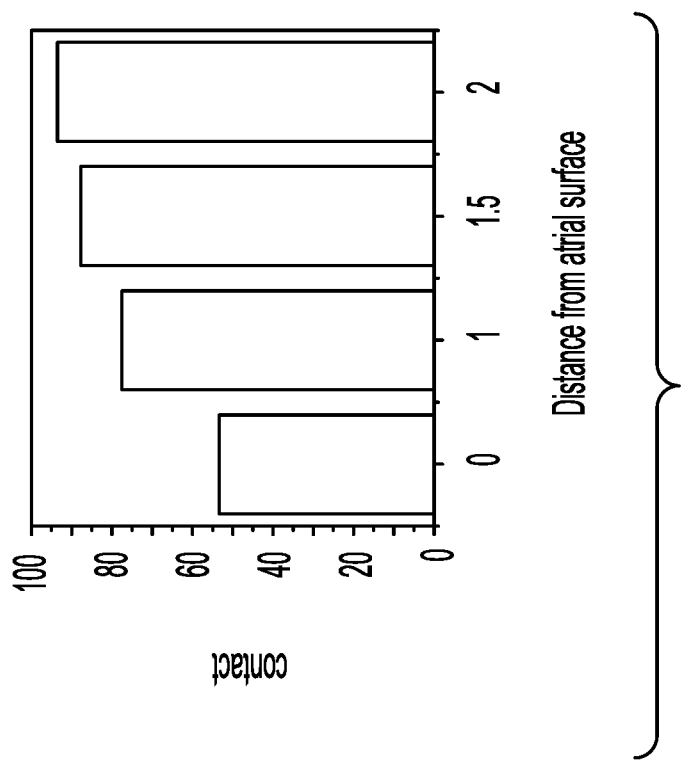
Figure 27B:
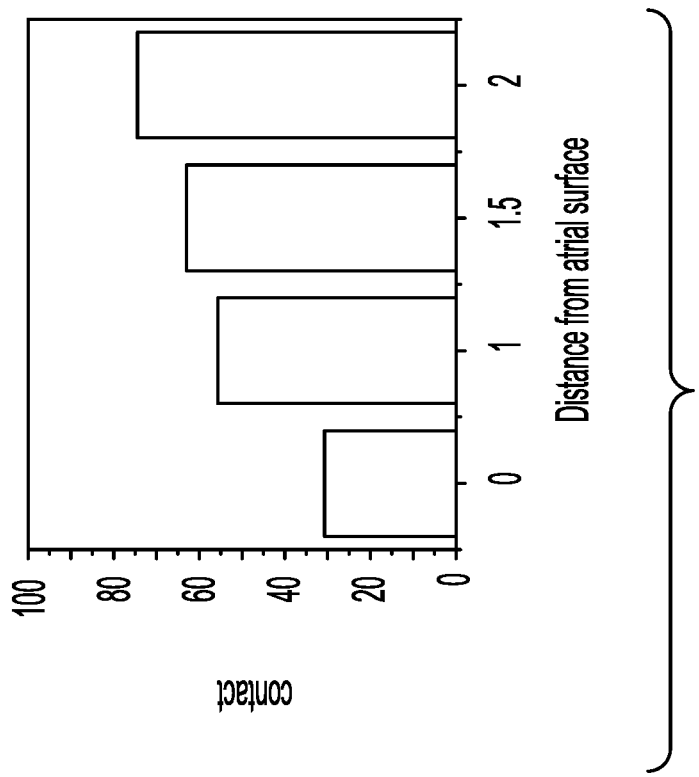
FIGS. 27A and 27B depict further example experimental data showing the percentage of the sensors of the soft-robotic sensor arrays shown in FIGS. 26A and 26B respectively when compared to the distance of the sensor arrays from the atrial surface, in accordance with one or more potential implementations.
Figure 27A:
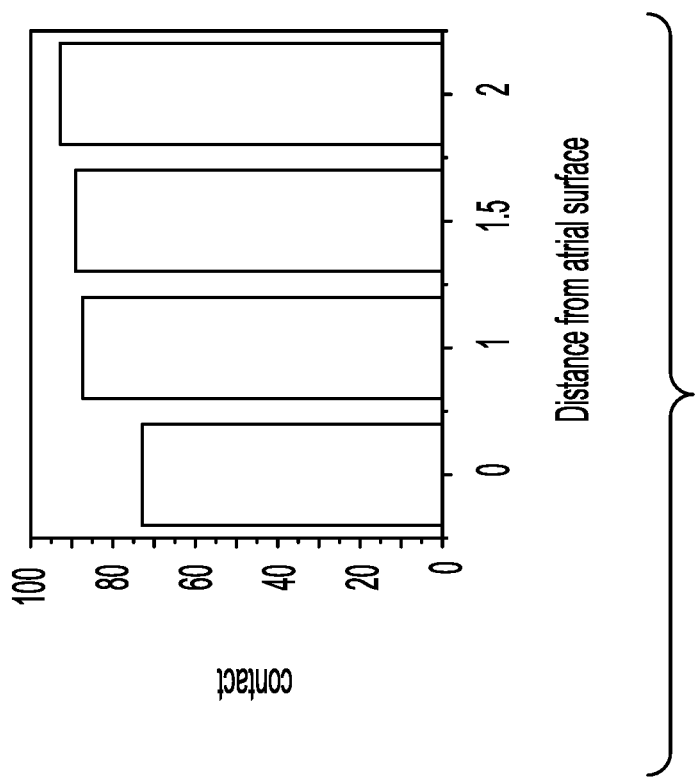

Durability Analysis of Stretchable Electronics Integrated Soft Actuators—Two separate experiments were conducted to evaluate the durability of the SRSAs. These results are shown in FIGS. 22A through 23C. In one experiment, one leg of the SRSA cage was actuated multiple times, and the resulting conductivity of the individual sensor traces was subsequently assessed (Signatone probe station, Tektronics 4200 parameter analyzer), as shown in FIG. 22A. The actuation was carried out by applying a pressure of 10 psi (68.95 kPa), which yielded a level of overall actuation consistent with those observed in the device and repeated for 100 iterations to evaluate the long-term durability of the electronics under repeated loading and deformation. For each of the electrodes, the current-voltage relation (I-V) sweep was recorded, and the resistance values were plotted as shown in FIG. 22A. The values remain within the SD even after 100 iterations, showing excellent durability of the stretchable electronics. Micro-CT (μ-CT) images and volume-rendered segmentations of individual linear SRSA are shown in FIG. 22B; the inset shows the SRSA. One reason these designs are able to demonstrate this type of durability is the low strain actuator design used. To understand the local strain observed in the sensor arrays themselves, strain in the copper traces along the length of the stretchable electronics was evaluated experimentally using confocal imaging, and FEA simulations (ANSYS workbench 19) were performed to validate these results. Note that maximum deformation occurs in the pockets that are along the length of the actuator legs. The pockets are part of the linear actuator design applied here, which allow for low strain actuation. They are formed by patterning the sacrificial PVA layer in a manner to allow the TPU to fuse in regions of the actuators, such that it subsequently inflates in discrete pockets. This can be clearly observed in FIG. 22B. This pocket section is considered to measure maximum strain in both experiments and simulations. To evaluate the strain experimentally, confocal images of the SRSA in both its non-actuated and actuated states were recorded. The average strain in each section of the traces was calculated using the deformation values between the two states. FEA analysis was con-ducted using the static structural module of ANSYS workbench. A hyperplastic model was defined as discussed in an earlier paper, and the balloon was actuated by applying a uniform pressure loading of 10 psi (68.95 kPa). Comparison between experimental and simulated results is shown in FIGS. 23A-23C. FIGS. 23A through 23C depict negligible strain along the length of the traces in the actuated state. The strain is maximum at the ends of the pocket region. We believe that this is due to the constraint that is provided based on the design of these actuators. However, this maximum strain is well within the de-sign limits for copper, thereby allowing these stretchable electronics to go through many actuation cycles. The alignment between experimental observation and simulation provides insight into the robustness and durability of these designs.

In vitro voltage mapping evaluations were performed on a single array of sensors (16 sensors, associated with a single actuator leg) using a cardiac tissue phantom. This demonstrates the sensors ability to read electrograms effectively. Referring briefly now to FIGS. 22A through 23C, the plot shown in FIG. 22A shows resistance as a function of actuations for a single actuator. The actuation was carried out at 10 psi (68.95 kPa). Inset shows the probe station used to measure resistance using an I-V sweep. FIG. 22B shows μ-CT images and volume-rendered segmentations of actuated linear SRSA are shown. FIGS. 23A, 23B, and 23C show an actuation pocket where maximum deformation takes place is simulated using ANSYS workbench. Strain values are compared between confocal images for an actuated pocket and that obtained from FEA analysis.

μ-CT conformability experiments—The overall goal of creating SRSAs with active soft actuators is to provide designs for sensor arrays that have the ability to conform to complex patient anatomies. Several commercial spline-based catheters are being developed for improved treatment of AFib with better con-formability. Among these, two representative examples, CONSTELLATION (Boston Scientific, MA) and FIRMAP (Abbott, IL), are discussed. CONSTELLATION (Boston Scientific, MA) catheter, which is more widely used, has several drawbacks including interspline bunching resulting in loss of coverage and contact and the lack of electrode poles proximally resulting in loss of septal coverage. To determine conformability, a simplified version of the left atrium segmented model can be used. Electrodes within 10 mm of the left atrium geometry were projected onto the geometry and marked as covering an area having a radius of 10 mm. Thus, the total atrial coverage achieved by the electrodes is calculated as a percentage of left atrium geometry surface area excluding the vascular and valvular structures. The average conformability using these catheters was ~50%. FIRMAP (Abbott, IL) catheters were designed as improvements over CONSTELLATION (Boston Scientific, MA) catheters. They have stiffer splines intended to minimize distortion and bunching. Electrode spacing is also increased with more proximal electrodes aiming to improve left atrial septal coverage. However, even with these improvements, they showed an average conformability of ~76% in the left atrium. Overall, conventional catheters are limited by electrode position, poor tissue contact, and spline bunching, which leads to poor electrical coverage within the left atrium. To assess the conformability of SRSAs, they were deployed in four patient-specific 3D printed left atria and actuated at 10 psi (68.95 kPa) to obtain its final configuration within the left atrium. µ-CT images (Siemens Inveon Multimodality Scanner) and volume-rendered segmentations (Mimics 19) of deployed SRSAs were used to analyze its conformability. The results are shown in FIGS. 24A through 27B. The top row of FIGS. 24A, 24B, 26A, and 26B show the SRSA cage deployed into the 3D printed atria via a mock catheter through the puncture made in the foramen ovale in the patient's septal wall. The SRSA cage conforms to the atrial surface effectively and shows no spline bunching (e.g., the individual linear actuators that form the SRSA cage were evenly distributed within the atria). Using mesh Boolean operations, the regions of intersections were obtained for each of these atria. Signals may be detected by the sensors at distances greater than 2 mm from the atrial surface. Considering these values, we color-coded different distances from 0 to 2 mm analogous to a thermal heatmap with the spectrum ranging from red to blue. These heatmaps (depicted as the bottom row in FIGS. 24A, 24B, 26A, and 26B) are superimposed on the SRSAs (depicted as the middle row in FIGS. 24A, 24B, 26A, and 26B) to show regions that are in direct contact with the atrial tissue.

FIGS. 25A, 25B, 27A, and 27B depict graphs showing the proportion of sensors within a given distance from the atrial surface are plotted for each atrium. The graphs in FIGS. 25A and 25B correspond respectively to the devices in FIGS. 24A and 24B, and the graphs in FIGS. 27A and 27B correspond respectively to the devices in FIGS. 26A and 26B. For these calculations, sensors that were not near tissue because they were adjacent to anatomic features such as the pulmonary veins or the left atrial appendage were ignored. SRSAs show an average conformability of ~85 to 90% for these randomly chosen patient-specific 3D printed patient atria. Atrium 4 shows the least conformability of 75%. This may be associated with the buckling of the SRSAs that can be clearly observed from the figure. Designs that mitigate this type of buckling or creating cages with appropriate sizing may represent a strategy to further increase the conformability of these devices. To address the dynamic motion of the device, we deployed it in the left atria of an excised porcine cadaver (unfixed tissue) and used a pulsatile flow loop (Shelley Medical) to produce realistic flow and deformations. The SRSA shows excellent conformability under dynamic flow conditions.

Referring briefly now to FIGS. 24A through 27B, an SRSA is deployed in four patient-specific 3D printed left atria (e.g., as shown in FIGS. 24A, 24B, 26A and 26B), and the µ-CT images and volume-rendered segmentations are shown. The heatmaps in the middle rows of the aforementioned figures indicate the distance of SRSA from the atrial surface. This can range between 0 and 2 mm with the spectrum moving from red to blue. Accounting for the voids in the geometry of the left atrium (mitral valve and pulmonary vein), the percentage of number of sensors in contact is plotted as a function of distance for each of the atria. An average conformability of ~85 to 90% was observed Conclusion—In this study, SRSAs are described that exhibit excellent mechanical durability and conformability when deployed with-in patient-specific 3D printed left atria. The method used to create these SRSAs illustrates a technique for integration of soft robotics and flexible electronics for medical applications, especially those deployed via a minimally invasive catheter. We demonstrated the mechanical durability of these devices by showing that sensors could undergo 100 cycles of actuation without reduction of performance. Furthermore, simulations were performed to assess the strain in electronics, which showed good match with the experimental values. SRSAs were deployed using a 13.5-Fr mock catheter into patient-specific soft 3D printed left atria (soft materials mimicking the atrial tissue) to analyze its conformability. SRSA shows an average conformability of ~85 to 90% within these atria. A method is described for scalable fabrication and integration of flexible electronics that provides a versatile approach for creating a wide variety of complex geometry actuator/sensor arrays that are broadly applicable. This enables development of efficient devices for better treatment of AFib and cardiac arrhythmias.

Materials and Methods—Each step along with the dimensions of individual components is designed considering the integration of stretchable electronics. To fabricate the SRSAs, we first laser cut sheets of PVA into their de-sired 2D geometry and sandwich it between two layers of TPU. PVA can be used for two purposes: (i) to prevent the bonding of the TPU layers and (ii) to act as a sacrificial layer and facilitate a path for the flow of the liquid (viz. water) during hydraulic actuation. The overall thickness of the inflatable frame can be varied based on the number of layers of TPU used. Before integrating the flex-PCB sensor arrays with the soft robotic actuators, a post-processing was carried out on the stretchable electronics with a unique laser-cutting step, as described herein above. An additional layer of TPU is heat-pressed on top of the stretchable sensor array to encapsulate them. Windows are laser cut to expose the sensor pads themselves.

For balloons deployed in patient atria, a somewhat more complex fabrication approach can be used to ensure that the hydraulic in-put was in line with the device itself, allowing it to be deployed via a catheter. The inflatable frame is fabricated in two parts, the hub and the legs. In this step, the TPU and PVA sheets are laser cut to the desired configuration. In step 3, before integrating the electronics with the laser-cut legs, a post-processing was carried out on the stretchable electronics with a unique laser-cutting step. Stretchable electronics, after post-processing, are aligned with PU sheets with laser-cut windows that expose the electrodes when in con-tact with the left atrial tissue. This also serves as the topmost layer of the final stack up. In the next step (step 4), the precut legs are integrated with windows and electronics using a heat press (280° F. for 600 s). Subsequently, laser-cut TPU and PVA forming the hub are also heat-pressed under the same conditions. In step 5, the heat-pressed hub and legs are integrated together to form the final balloon. Adaptors crafted out of PVA are used in this process to prevent leaks and ensure contact between these parts. Once the complete SRSAs are fabricated, the sacrificial PVA layer is removed by perfusing the actuators with water.

Although various implementations and geometries of SRSAs have been described in this section, it should be understood that any particular geometry, configuration, or of a flexible actuator can be used in the systems, devices, or methods as described herein. For example, certain actuator geometries may be suitable for certain inertial body structures, such as organs, veins, arteries, glands, tubes, cavities, or any other type of biological structure. In addition, the use of different sensors may be suitable for recording or registering signals of interest, and corresponding flexible electronic components may be integrated into the flexible electronic devices (and methods of manufacture) described herein above. As described herein and in the following sections, a variety of different sensing technology can be integrated with the SRSAs described in this section to accomplished a desired mapping, ablation, or sensing of biological attributes of a tissue, an organ, or a patient C. Conformal, Non-Occluding Sensor Arrays for Internal Organ Structure Mapping Sensing, and Ablation The systems and methods described herein provide a means to measure signals from a tissue cavity or organ of a patient using an expandable measurement device. The expandable measurement device can be actuated by introducing a fluid into the cavities of the measurement device, causing the measurement to inflate and conform to the walls of the cavity or organ that is being measured. The measurement devices described herein can be constructed from one or more beams of flexible substrate to provide support and force electrodes or other sensors against the walls of the tissue being measured without occluding or preventing the flow of blood. One example of organ measurement described herein above is the measurement of the atria of the heart. Using a catheter and a transseptal puncture technique, the measurement device described herein can be introduced to the left atrium of the heart and subsequently actuated to measure signals and detect cardiac arrhythmia.

Detailed implementations of the measurement devices, constructed utilizing the techniques described herein above, are provided in this section. As described herein, the measurement devices are constructed from biocompatible polymers integrated with flexible circuitry, which can include electrodes, sensors, and other flexible circuitry. The measurement devices can be constructed utilizing the processes described herein above using the post-processing techniques described herein above in conjunction with FIGS. 19 and 20. Although the measurement devices described in prior sections are shown used in atrial measurement scenarios, the measurement devices described herein can be utilized for measuring signals from any tissue structure in a patient, including external structures like the skin.

Figure 16:
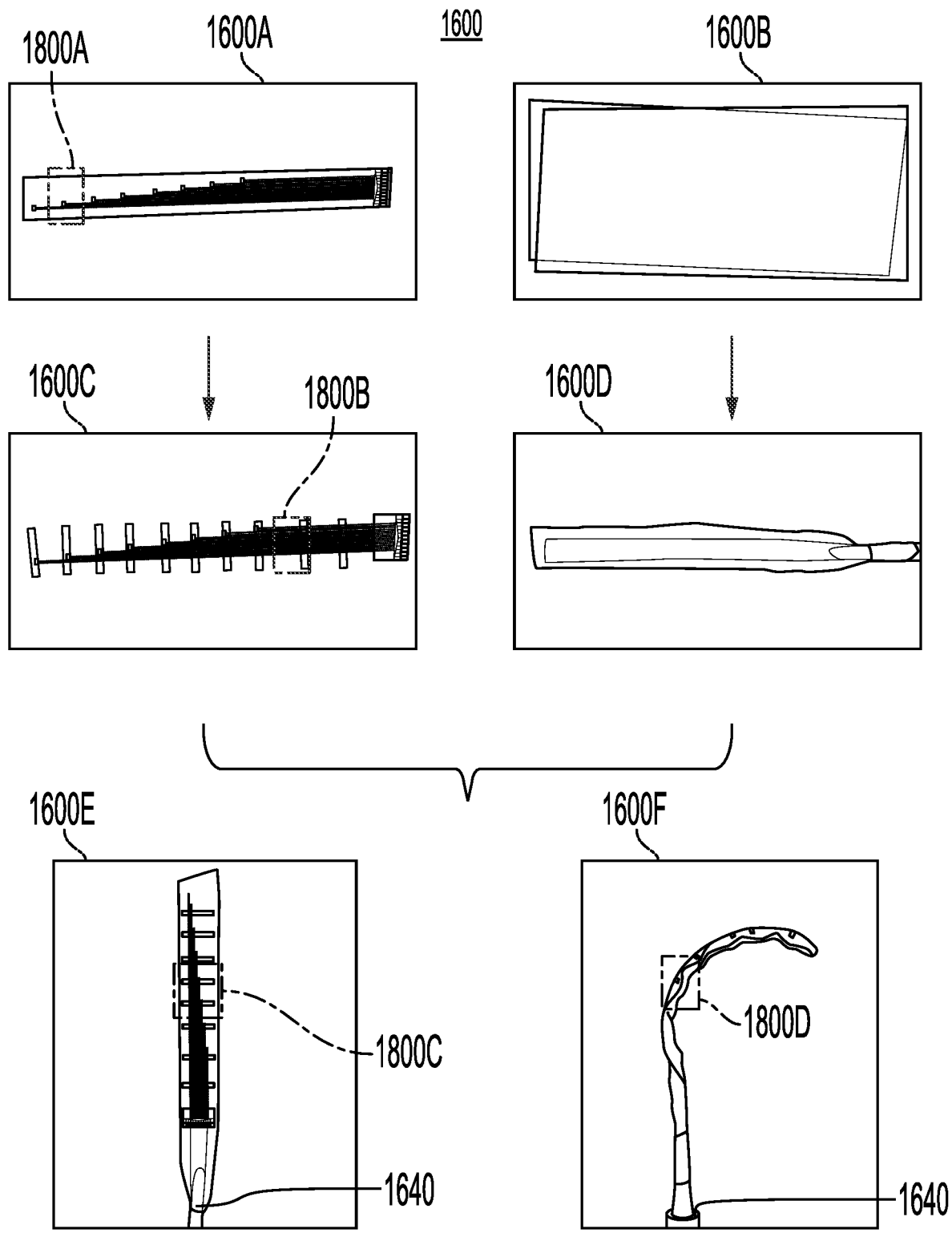
FIG. 16 depicts various views of an example construction of a soft-robotic sensory array, in accordance with one or more potential implementations.

Referring now to FIG. 16, depicted are various views of an example construction of a soft-robotic sensory array, in accordance with one or more implementations. The SRSA can be a device having one or more layers of thermoplastic substrate that are coupled to a metallic circuitry layer. The metallic circuitry layer can first be created as traces on a flex PCB, and subsequently laser etched, as described herein above, leaving the traces for integration with the thermoplastic substrate. View 1600B of FIG. 16 shows example sheets of thermoplastic substrate used in the construction of a conformable measurement device. Said substrate sheets can be formed into a desired shape based on the tissue structure for which the measurement device will be used. As shown in views 1600A, 1600C, and 1600D, the metal layers extracted from the flex PCB can be affixed (e.g., via heat pressing, adhesives, or other coupling means) to a surface of one of the polymer sheets.

One or more of the polymer sheets that make up the device can have a surface that is coupled to a metal layer forming a conductive trace. The metal layer can also include electrode pads that can receive signals from tissue walls once the pads are exposed via one or more openings (e.g., openings cut via laser cutting or another type of cutting technique, etc.). The substrate sheets depicted in views 1600B, 1600D, 1600E and 1600F can include any type of elastomer, including a urethane polymer, a polyurethane polymer, a copolymer, silicone, or any other type of elastomer. Portions of the metal layer (e.g., including one or more traces and pads, etc.) can be embedded within portions of flex PCB that remain from the laser etching process described herein above. The flex PCB can be coupled to the surface of the substrate sheet in the same manner as the metal layer (e.g., via heat pressing, an adhesive, or any other type of coupling process suitable for metal and elastomers, etc.). Once coupled to the layer of thermoplastic substrate, the electrode pads of the metal layer can be exposed via one or more openings from the opposite surface of the substrate layer. In this way, the opposite surface of the substrate layer (e.g., that exposing the pads) can be directly exposed to biological tissue. Signals generated by the biological tissue can be detected by the exposed pads, and transmitted to one or more sensors or monitoring devices via the conductive traces in the metal layer. Because the metal layer is coupled to the opposite surface, it is largely protected from any other biological signals generated by the tissue being measured.

A beam (e.g., the beam of the measurement device depicted in view 1600F, etc.) can include a second polymer substrate that is coupled, either directly or via one or more intermediate layers, to the other thermoplastic substrate having the metal layer. The second thermoplastic substrate can be formed from the same material as the first thermoplastic substrate, that is, any type of elastomer (e.g., a urethane polymer, a polyurethane polymer, a copolymer, silicone, any other type of elastomer, etc.). The second sheet of thermoplastic substrate can form a cavity, or hollow portion, between the first thermoplastic substrate and the second thermoplastic substrate. The cavity can be used to inflate the measurement to conform to a desired tissue structure. The shape, thickness, and density of the thermoplastic substrate layers can be selected to shape the measurement device according to the structure of what is being measured. For example, in a circumstance where signals from the walls of a chamber, such as an atrium of a heart, are being measured, the beams that make up the measurement device can be formed with a curve to match the curve of the atrium chamber. An example beam with aforementioned cure is depicted in view 1600F of FIG. 16.

Figure 18A:
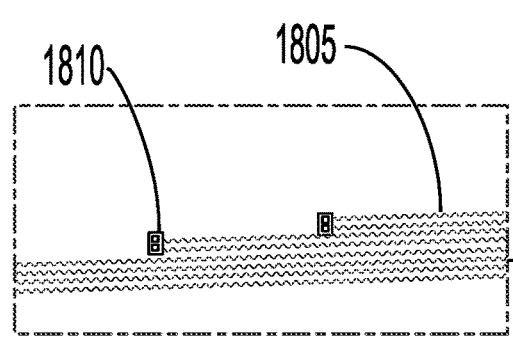
FIGS. 18A, 18B, 18C, 18D, and 18E depict various close-up views of the soft-robotic sensor array components depicted in FIGS. 16 and 17A, in accordance with one or more potential implementations.
Figure 18B:
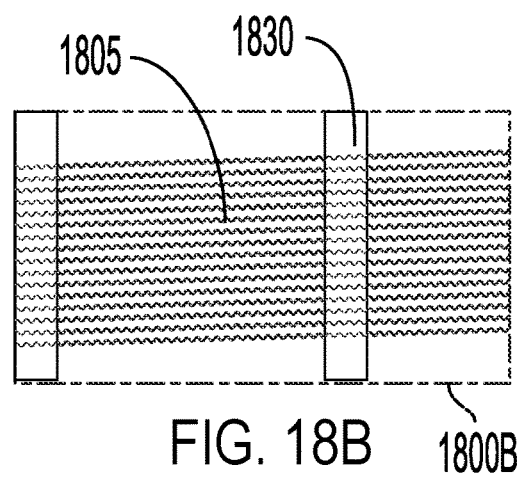

In further detail of the measurement device construction, and referring now to FIG. 18A, depicted is a view 1800A of the metal layer, forming conductive traces 1805 and electrode pads 1810. The metal layer can be formed from any suitable conductive layer, including conductive polymers, copper (e.g., copper used in PCB manufacture of traces, etc.), a copper compound, nickel, silver, or gold, among others. The electrode pads can be treated with a chemical that prevents corrosion when exposed to fluids internal to the body, thereby avoiding signal attenuation or depositing reactive metal oxides in a patient. In some implementations, the electrode pads 1810 can be plated with a non-reactive but highly conductive metal, such as gold, to achieve a similar outcome. Referring now to FIG. 18B, depicted are the same traces 1805 but embedded within a portion of flex PCB 1830. The portions of flex PCB can be coupled to a surface of a thermoplastic substrate as described herein above. The flex PCB can be a thin printed circuit board, such as a fiberglass or other type of non-conductive polymer that can be used to provide additional structure to the measurement device. Additional electronics or sensors can be provided either as part of the metal layer or embedded on the portions of flex PCB 1830. Some example sensors (not pictured) can include a force sensor, a shear force sensor, a fluid flow sensor, an ultrasound senor, a thermal sensor, a position sensor, an electrocardiogram sensor, or an electrochemical sensor. Such sensors can be integrated, or form a part of, one or more circuits disposed within the metal layer or embedded on the flex PCB 1830. In some implementations, the traces 1805 can transmit signals detected by the sensors to an externa measurement device.

Figure 18C:
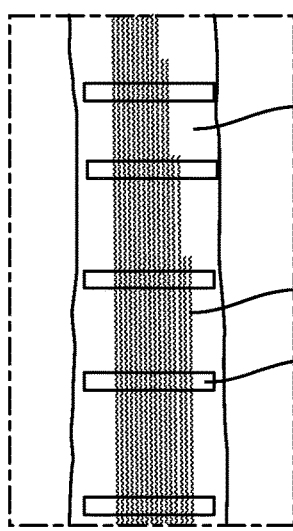

Referring now to FIG. 18C and in greater detail of the first substrate layer, a view 1800C of the first substrate layer 1820, coupled to the metal layer having traces 1805 embedded within portions of flex PCB 1830, is depicted. As shown in the view 1800C, the traces 1805 formed in the metal layer can terminate at different lengths. In some implementations, the traces can terminate in pairs, forming a bi-polar electrode pair using the conductive pads 1810. In some implementations, the conductive pads 1810 can form a mono-polar electrode, where the signals detected by the conductive pad 1810 are referenced to an external ground node. The conductive pads 1810 can terminate the traces, such that the sensing circuit is completed by an external tissue surface making contact with each of the conductive pads 1810. The traces 1805 can terminate at different lengths along the outer surface of the thermoplastic substrate 1820 to provide electrode coverage along the length of the measurement device. The number of electrodes can be a function of the number of conductive traces that can be placed on the metal layer. Given that the traces 1805 have a minimum thickness and width to maintain structural integrity even when actuated, the number of traces possible on a substrate can be a function of the area of the substrate. For example, for a very large substrate, a large number of electrodes can be placed on its surface. In contrast, a smaller substrate may have less space for electrodes and traces.

Figure 18D:
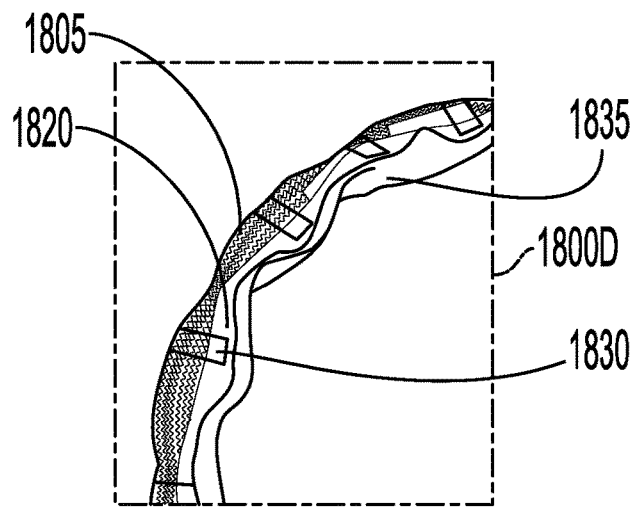

Referring now to FIG. 18D and describing an aspect of the measurement device in greater detail, depicted is a view 1800D that includes both the first and the second thermoplastic substrate. The measurement device is depicted as actuated, or inflated, to indicate the presence of the inflatable cavity formed in the space between the first substrate and the second substrate. As shown in view 1800D, the second substrate 1835 is coupled to the first substrate 1820, either by a heat-pressing process, an adhesive, or other means of coupling the first substrate to the second substrate. In some implementations, the second substrate 1835 can be first substrate 1820 folded over onto itself, and sealed to form the cavity region. The conductive traces can be on the surface of the substrate that faces the cavity, and thus protected from any tissue, fluids, or biological matter that might contact the outer surface of the measurement device. The traces 1805 can be exposed to such elements at the conductive pads 1810 via one or more openings in the substrate 1820. In some implementations, the conductive pads 1810 can be embedded in the portions of flexible PCB 1830, and exposed in a similar fashion via the openings in the substrate 1820.

Figure 18E:
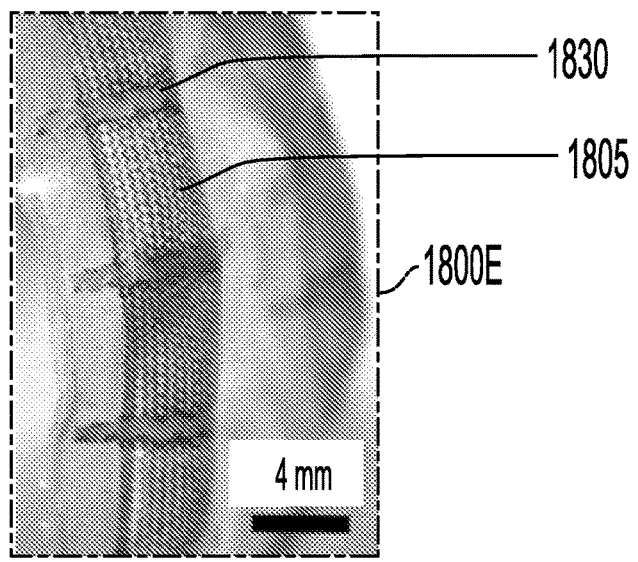

As depicted in view 1800D of FIG. 18D and similarly in a photographic view of a beam 1800E in FIG. 18E, the measurement device can be inflated, or actuating, using one or more fluids. As the traces 1805 and the substrates 1820 and 1835 are flexible, a fluid can be introduced into the cavity formed between the substrates 1820 and 1835 to increase the size of the measurement device. The shape of the substrates 1820 and 1835 of the measurement device can be selected such that when the device is inflated, it conforms to the structure of the region of the patient that is being measured. The fluid can be provided to fill the cavity between the substrates 1820 via a lumen coupled to an inlet portion of the measurement device. The lumen can be provided as part of a catheter used to introduce the measurement device to a patient. Although the configurations of FIGS. 18A-18E are depicted as having a metal layer on only one of the substrates 1820 of the measurement device, it should be understood that additional metal layers can be disposed within the second substrate 1835 of the measurement device, with sensors, contact pads, and flexible PCB portions similar to those described above. For example, the second substrate 1835 can include one or more sensors, which may be one or more of a force sensor, a shear force sensor, a fluid flow sensor, an ultrasound senor, a thermal sensor, a position sensor, an electrocardiogram sensor, or an electrochemical sensor. The types of sensors disposed throughout the measurement device may be selected based on the measurements to be performed or the position on the measurement device that the sensor is disposed.

Referring back now to FIG. 16, depicted are views 1600E and 1600F that show the measurement device in an unactuated (e.g., uninflated) state and an actuated state, respectively. As shown in view 1600E, the unactuated measurement device can be substantially flat, with the cavity region formed between the first substrate empty. The inlet portion 1640 is depicted at the bottom of the measurement device, and is coupled to a lumen that can provide fluid to expand the cavity and actuate the device, as depicted in view 1600F. The fluid used to actuate the device can be provided by a pump, such as a manual or automatic pumping mechanism. The fluid can be transported from a fluid reservoir using the pump. The fluid can include, for example, a liquid such as water, or a gas such as air, nitrogen, or any other type of fluid that can be safely introduced to a patient. The amount of fluid introduced to the measurement device can be varied to cause the measurement device to enter different states of actuation. Certain signals or arrangements may require different levels of conformity by the measurement device.

Referring back now to FIGS. 18A through 18E, as depicted, the traces 1805 are serpentine traces, such that if the surface area of the substrate expands, the traces can also expand without severing their electrical connection to the conductive pads 1810 or any sensors or other devices. In some implementations, conductive traces 1805 can form a different shape that accomplishes a similar goal, such as a zig-zag pattern. In some implementations, the conductive traces 1805 can be made from a stretchable and conductive material, and therefore no such serpentine pattern may be needed to maintain the structural integrity of the trace when the measurement device expands. Although serpentine traces are shown here, it should be understood that other stretchable trace configurations are possible, including linear traces, curved traces, or zig-zag traces, among others.

By providing or removing the fluid from the measurement device, the device can achieve different structural properties (e.g., rigidity, flexibility, etc.) that can be suitable for different applications. For example, to prevent buckling in certain cavities, it may be advantageous to inflate the measurement device to such that it becomes more rigid. Likewise, when rigidity may not be required (or may interfere with an organ under measurement, etc.) less fluid can be used to actuate the device. The inlet portion can also serve as the place where the traces 1805 depicted in FIGS. 18A-18E are electrically coupled to a portion of a catheter device, which can transmit signals received via the contact pads to an external monitoring device. The external monitoring device can record the signal in computer memory. In some implementations, the traces on the measurement device can transmit signals to a wireless transponder in wireless communication with one or more external monitoring devices. In such implementations, the measurement device may be a permanent or semi-permanent measurement device that transmits signals wireless on a periodic, batch, or relatively continuous basis.

Figure 17A:
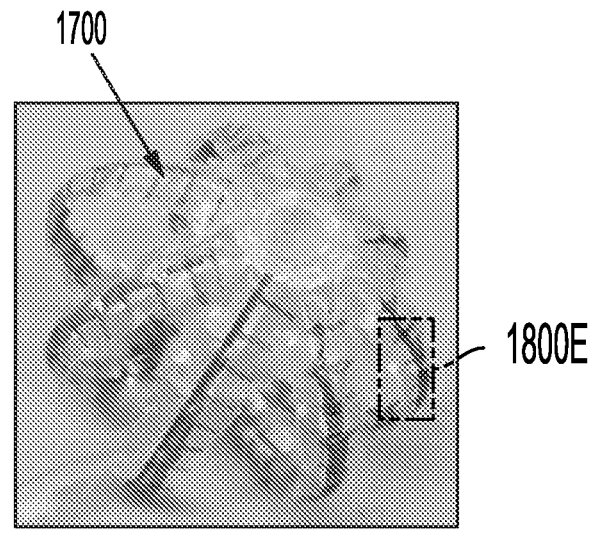
FIG. 17A depicts an example balloon with integrated electronics, in accordance with one or more potential implementations.

As described herein, the measurement device shown in FIGS. 16 and 18A through 18E can be formed as a beam of a larger measurement structure. For example, the view 1600F of FIG. 16 depicts one such beam coupled to a single inlet portion. However, it should be understood that the techniques described herein can be used to construct measurement devices having multiple beams, which can be fluidly connected at junctions formed between the beams. One such implementation of a measurement device is shown in FIG. 17A. As shown in FIG. 17A, the measurement device 1700 is made up of several measurement beams 1800E, which is depicted in greater detail in FIG. 18E. As depicted, the measurement device 1700 includes several beams 1800E, each of which can include their own substrates, metal layers, traces, electric contacts, and sensors, as described herein above. The catheter device coupled to the end of the measurement device 1700 can receive signals from the conductive pads or sensors disposed on each of the beams 1800E. The inlet portions of the beams 1800E can each be connected to a single lumen that provides the fluid to actuate the device. In some implementations, each of the inlet portions of the beams 1800E of the measurement device 1700 can have its own lumen, allowing the beams of the device to be actuated independently. Additional fluidly connected junctions can be formed between the beams 1800E to evenly distribute flow of the fluid throughout the measurement device 1700. For example, the end of each beam opposite the end connected to the lumen can be fluidly connected to one another, such that the fluid flows through the device uniformly.

Although the measurement device 1700 depicted in FIG. 17A is shown as a star configuration (e.g., where the beams, when uninflated, cause the device to appear as a star; similar to the configuration depicted in FIG. 10A), it should be understood that any three-dimensional configuration of beams are possible. For example, the three-dimensional structure formed by the beams can include a star configuration, a sphere configuration, a linear configuration, a conical configuration, or a cylindrical configuration, among others. Examples of the sphere configuration is depicted in the top image of FIG. 3A. Further, although the beams depicted in FIGS. 16, 18A-18E are shown to be substantially linear, it should be understood that the beams can take on any shape suitable for insertion into a patient via an insertion device, such as a catheter. In circumstances where the device is used external the patient, additional configurations are possible that cause the device to wrap around structures of interest, such as a sleeve or other tube-like structure.

Given that the measurement device can have many beams and many junctions between beams, mesh-like configurations of the measurement device can exist that conform to a side-wall of an organ of interest. Tube-like configurations can also be provided to allow mapping or sensing of arterial or veinal walls. It should be understood that additional configurations are possible, including any number of traces, electrode pads or pairs, or sensors present in any position of the measurement device. In general, a measurement device having a larger surface area covered with more sensors can detect signals from more locations on a tissue surface than a smaller measurement device. The three-dimensional structure of the measurement device can conform, when expanded, to regions of biological tissue that would otherwise be challenging or impossible to reach using conventional sensing technology. In addition, the structure of the device can be incrementally modified for different signal requirements by precisely controlling the fluid used for device actuation.

Figure 28:
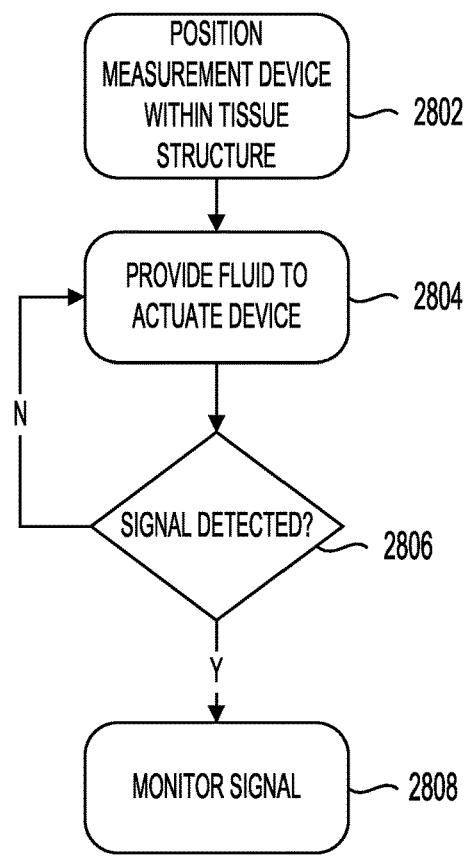
FIG. 28 depicts an example method of detecting signals using an expandable measurement device, in accordance with one or more potential implementations.

Referring now to FIG. 28, depicted is an example method 2800 of detecting signals using an expandable measurement device, in accordance with one or more implementations. The method 2800 can be performed, for example, as part of a surgical procedure to detect signals from an internal organ of a patient. The internal organ can be a chamber of a heart, or another type of organ, blood vessel, or cavity from which signals can be detected using electrodes. The method can include positioning a measurement device within an internal tissue structure of a patient (STEP 2802). The method can include providing a fluid to actuate the measurement device (STEP 2804). The method can include determining whether a signal is detected after providing the fluid (STEP 2806). The method can include monitoring one or more signals using the measurement device (STEP 2808).

Figure 17B:
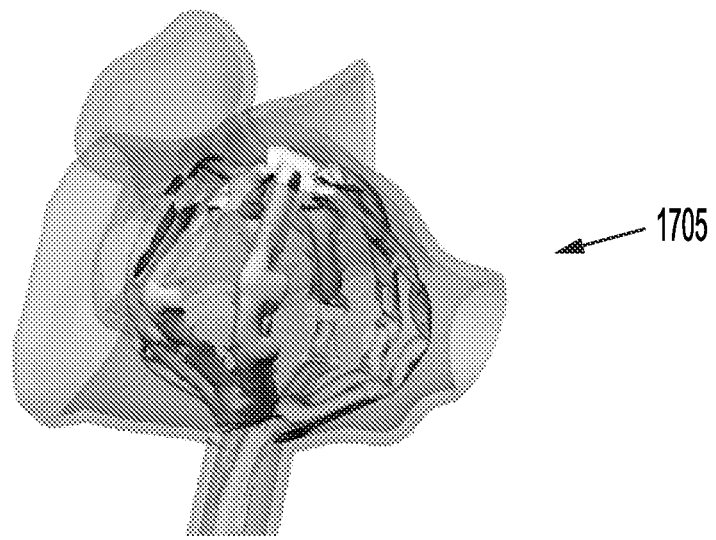
FIG. 17B depicts an example rendering of the balloon of FIG. 17A deployed in a left atrium, in accordance with one or more potential implementations.

The method 2800 can include positioning a measurement device within an internal tissue structure of a patient (STEP 2802). The measurement device can be a measurement device similar to that described herein above in conjunction with FIGS. 16, 17A-17B, and FIGS. 18A-18E. As described above, the measurement device can be positioned within a patient as part of a surgical procedure. The measurement device can be positioned to be substantially centered within the organ or chamber that is to be measured. For example, the measurement device can be introduced into the left atrium of a heart of a patient using a transseptal puncture procedure. In a transseptal puncture procedure, the measurement device can first be in a deflated, or unactuated, state where the cavities in the one or more beams of the measurement device are deflated. The device can be introduced to the right atrium of the heart in a surgical procedure via the femoral vein, and a fence catheter can be used to turn the measurement device 90 degrees. The atrial septum can be punctured, and the measurement device can be pushed from inside the right atrium to inside the left atrium of the heart. Other similar surgical procedures can be used to introduce the measurement device to other cavities, organs, or blood vessels in a patient. Because the beams of the measurement device provide substantial open space (e.g., as depicted in FIGS. 17A and 17B, the measurement device can make contact with the walls of the organ, blood vessel, or cavity of interest without occluding flow of blood through the cavity. This can allow for the precise measurement or internal signals without significantly impairing the biological function of the organ being measured.

The method 2800 can include providing a fluid to actuate the measurement device (STEP 2804). Once the measurement device, now in an uninflated or unactuated state, is positioned within the organ, cavity, or blood vessel of interest, the measurement device can be actuated to conform the device to one or more walls of the tissue under measurement. A lumen, attached to at least one of the catheters used to introduce the measurement device to the patient in (STEP 2802), can be used to provide a fluid to fill the cavities of the measurement device. In this way, the cavities in each of the beams of the measurement device can be filled with fluid to cause the measurement device to expand within the cavity (e.g., as shown in 1705 of FIG. 17B). As shown in FIG. 17A, the beams 1800E of the measurement device 1700 can be bent and fixed to one another to form a shape that corresponds to the tissue cavity of interest. As depicted in the render 1705 of FIG. 17B, the tissue cavity of interest can be the left atrium of the heart. However, it should be understood that other tissue cavities, organs, or blood vessels are possible to monitor using the method 2800. The shape of the beams of the measurement device 1700 can be chosen such that, when inflated or actuated using the fluid, the cavities inside the beams cause the beams of the measurement device to expand and press against the walls of the cavity or organ of interest without occluding the natural flow of blood within the cavity or organ. The measurement device can be actuated, for example, using a pump to pump a fluid, such as water, from a fluid reservoir through the lumen of the catheter and into the cavities of the beams of the measurement device. The pump can maintain a predetermined pressure, or provide a predetermined amount of fluid as indicated by a surgeon or other internal configuration setting. In some implementations, the amount of fluid provided by the pump through the lumen is determined based on the signals detected via the electrodes on the measurement device, as described herein below. The amount of fluid used to actuate the measurement device can be determined based on various factors, including one or more of a type of the internal tissue structure, a volume of the measurement device, or information from an image of the internal tissue structure.

The method can include determining whether a signal is detected after providing the fluid (STEP 2806). Once the measurement device is actuated, the electrode pads exposed via the openings in the substrate of the device can press up against, or be close enough to detect signals from, the cavity or organ of interest. In some circumstances, signals can be detected by electrodes or sensors disposed on the surface of the measurement device when the measurement device is a predetermined distance from the walls of the internal tissue structure. For example, in the left atrium of the heart, the measurement device may be able to detect signals from the wall of the heart even when the electrode pads are two millimeters way from the heart tissue. The electrodes exposed on the surface of the measurement device can be electrically coupled to sensors via stretchable traces disposed through the substrate of the measurement device, such as the traces 1805 as depicted in FIGS. 18A-18E. In addition, other types of sensors can be disposed throughout the substrate of the measurement device, such as force sensors, a shear force sensors, fluid flow sensors, ultrasound sensors, thermal sensors, position sensors, electrocardiogram sensors, or an electrochemical sensors, among others. The electrical traces, such as the electrical traces 1805 depicted in FIGS. 18A-18E, can transmit signals received from the tissue (e.g., or by the sensors in proximity to tissue or fluid flow, etc.) to a measurement device. For example, the catheter used to introduce the measurement device can include a plurality of transmission lines that are electrically coupled to the traces on the measurement device. In some implementations, the traces on the measurement device can transmit signals to a wireless transponder in wireless communication with one or more external monitoring devices. In such implementations, the measurement device may be a permanent or semi-permanent measurement device that transmits signals wireless on a periodic, batch, or relatively continuous basis.

The external monitoring device responsible for receiving the signals detected and transmitted by the measurement device can determine whether the measurement device requires additional actuation. In some implementations, a surgeon or other medical professional can make this determination based on the signals, or absence of signals, provided by the measurement device. For example, if the measurement device cannot detect signals from the tissue structure, it is likely that the beams of the measurement device are not in close-enough proximity to the tissue to detect signals. In such a case, the method 2800 can return to STEP 2804 of the method to provide additional actuation fluid to the measurement device until a signal condition is met (e.g., a number or percentage of electrodes on the measurement, above a predetermined threshold, can detect signals from the tissue, etc.). If the signal condition is met for proper measurement, additional actuation fluid may not be needed to retrieve useful signals from the measurement device, and the method can proceed to STEP 2808.

The method 2800 can include monitoring one or more signals using the measurement device (STEP 2808). Monitoring the signals can include recording the signals received from electrodes, sensors, or other measurement means coupled to the measurement device actuated in STEPS 2804 and 2806. For example, the signals monitored by the external monitoring device and received from the measurement device can include force values, shear force values, ultrasound values, temperature values, position values (e.g., for mapping the structure of an organ or cavity, etc.), electrocardiogram value (e.g., to detect cardiac arrhythmias, etc.), fluid flow values (e.g., such as blood flow rate, heart rate, etc.) or an electrochemical value (e.g., pH of blood, chemical detectors, etc.). These signals can be recorded by the external measurement device and stored in one or more data structures a memory of the external computing device.

Example embodiments may include:

Embodiment A: A device with improved structural conformity, comprising: a first polymer substrate having a first surface coupled to a conductive layer forming a conductive trace electrically coupled to a conductive pad exposed through a second surface of the first polymer substrate via an opening in the first polymer substrate; a second polymer substrate forming a first cavity between the first polymer substrate and the second polymer substrate; and a first inlet portion that receives a fluid that expands the first cavity causing the device to at least partially conform to an anatomical structure, wherein the conductive pad detects a signal from the anatomical structure.

Embodiment B: The device of Embodiment A, wherein the first polymer substrate, the second polymer substrate, and the first inlet portion form a first soft-electronic beam of a plurality of soft-electronic beams, and wherein the plurality of soft-electronic beams form a three-dimensional structure that conforms to the anatomical structure responsive to receiving the fluid.

Embodiment C: The device of either Embodiment A or B, wherein the three-dimensional structure formed by the plurality of soft-electronic beams is at least one of a star configuration, a sphere configuration, a linear configuration, a conical configuration, or a cylindrical configuration.

Embodiment D: The device of any of Embodiments A-C, wherein at least one of the first polymer or the second polymer comprise at least one of a urethane polymer, a polyurethane polymer, a copolymer, a silicone polymer, or an elastomer.

Embodiment E: The device of any of Embodiments A-D, wherein the conductive trace provides the signal detected by the conductive pad to a catheter that transmits the signal to an external measurement device.

Embodiment F: The device of any of Embodiments A-E, wherein the conductive trace is coupled to a portion of a flexible printed-circuit board substrate that is coupled to at least one of the first polymer substrate or the second polymer substrate.

Embodiment G: The device of any of Embodiments A-F, wherein one or more of the conductive pad or the conductive trace is electrically coupled to a sensor comprising at least one of a force sensor, a shear sensor, an ultrasound senor, a thermal sensor, a position sensor, an electrocardiogram sensor, or an electrochemical sensor.

Embodiment H: The device of any of Embodiments A-G, wherein the sensor is coupled to at least one of the first polymer substrate, the second polymer substrate, or a flexible printed-circuit board layer coupled to the conductive layer and to at least one of the first polymer substrate or the second polymer substrate.

Embodiment I: The device of any of Embodiments A-H, wherein the second polymer substrate is coupled to a second conductive trace electrically coupled to a second conductive pad; and wherein the second conductive pad is coupled to a second sensor comprising at least one of a force sensor, a shear sensor, an ultrasound senor, a thermal sensor, a position sensor, an electrocardiogram sensor, or an electrochemical sensor.

Embodiment J: The device of any of Embodiments A-I, wherein the conductive trace is patterned in at least one of a serpentine pattern, a linear pattern, a curved pattern, or a zig-zag pattern, wherein the conductive trace stretches in response to the first inlet portion receiving the fluid that expands the first cavity.

Embodiment K: A system, comprising: an expandable measurement device having a plurality of beams, each of the plurality of beams having a first end, a second end, and a cavity portion, wherein the first end of each of the plurality of beams are coupled to the lumen and receive a fluid to fill the cavity portion; a plurality of electrodes disposed on a first surface of each of the plurality of beams; and a plurality of transmission lines, each of the plurality of transmission lines electrically coupled to a respective one of the plurality of electrodes.

Embodiment L: The system of Embodiment K, wherein the second end of each the plurality of beams are fluidly coupled to one another at one or more junctions.

Embodiment M: The system of either Embodiment K or L, further comprising a lumen configured to provide the fluid from a fluid reservoir, wherein different amounts of fluid provided by the lumen causes the cavity portions of each of the plurality of beams to expand by varying degrees to conform to different anatomical structures.

Embodiment N: The system of any of Embodiments K-M, wherein each of the plurality of beams include a substrate comprising at least one of a urethane polymer, a polyurethane polymer, a copolymer, a silicone polymer, or an elastomer.

Embodiment O: The system of any of Embodiments K-N, wherein the plurality of electrodes each detects a signal from one or more surfaces of an anatomical structure, and wherein the each of the plurality of transmission lines transmits the signal detected by each of the plurality of electrodes to an external measurement device.

Embodiment P: A method of detecting signals using an expandable measurement device, comprising: positioning a measurement device within an internal anatomical structure of a patient, the measurement device comprising: a first polymer substrate having a first surface coupled to a conductive layer forming a conductive trace electrically coupled to a conductive pad exposed through a second surface of the first polymer substrate via an opening in the first polymer substrate, a second polymer substrate secured to the first polymer substrate and forming a first cavity between the first polymer substrate and the second polymer substrate, and a first inlet portion coupled to a lumen that receives a fluid that expands the first cavity; providing, via the lumen, a first amount of the fluid that causes the measurement device to expand by a volume corresponding to the first amount of fluid, wherein the conductive pad detects a signal from the internal anatomical structure via the opening responsive to expanding the first cavity; and monitoring, responsive to providing the first amount of the fluid via the lumen, using a measurement device, the signal detected by the conductive pad.

Embodiment Q: The method of Embodiment P, further comprising: determining that the signal from the internal anatomical structure is not detected by the conductive pad responsive providing the first amount of the fluid; and providing, responsive to the determination that the signal is not detected, a second amount of the fluid that causes the cavity to a size larger than the size of the cavity after providing the first amount of the fluid.

Embodiment R: The method of either Embodiment P or Q, wherein monitoring the signal using the measurement device further comprises measuring at least one of a force value, a shear force value, an ultrasound value, a temperature value, a position value, an electrocardiogram value, or an electrochemical value.

Embodiment S: The method of any of Embodiments P-R, wherein providing the first amount of fluid comprises determining the first amount of the fluid based on at least one of a type of the internal anatomical structure, a volume of the measurement device, or information from an image of the internal anatomical structure.

Embodiment T: The method of any of Embodiments P-S, wherein the internal anatomical structure is an atrium of a heart of the patient, and wherein positioning the measurement device within the internal tissue structure is performed using at least a transseptal puncture.

While this specification contains many specific implementation details, these should not be construed as limitations on the scope of any implementations or of what may be claimed, but rather as descriptions of features specific to particular implementations of the systems and methods described herein. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In some cases, the actions recited in the claims can be performed in a different order and still achieve desirable results. In addition, the processes depicted in the accompanying figures do not necessarily require the particular order shown, or sequential order, to achieve desirable results.

Having now described some illustrative implementations and implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed only in connection with one implementation are not intended to be excluded from a similar role in other implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation, and references to "an implementation," "some implementations," "an alternate implementation," "various implementation," "one implementation" or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms.

Where technical features in the drawings, detailed description or any claim are followed by reference signs, the reference signs have been included for the sole purpose of increasing the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. Although the examples provided herein relate to controlling the display of content of information resources, the systems and methods described herein can include applied to other environments. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

Having described certain embodiments of methods and systems, it will now become apparent to one of skill in the art that other embodiments incorporating the concepts of the disclosure may be used. Therefore, the disclosure should not be limited to certain embodiments, but rather should be limited only by the spirit and scope of the following claims.

What is claimed is:

1. A device with improved structural conformity, comprising:
    a first polymer substrate having a first surface coupled to a conductive layer forming a conductive trace electrically coupled to a conductive pad exposed through a second surface of the first polymer substrate via an opening in the first polymer substrate;
    a second polymer substrate forming a first cavity between the first polymer substrate and the second polymer substrate; and
    a first inlet portion that receives a fluid that expands the first cavity causing the device to at least partially conform to an anatomical structure,
    wherein the conductive pad detects a signal from the anatomical structure.

2. The device of claim 1, wherein the first polymer substrate, the second polymer substrate, and the first inlet portion form a first soft-electronic beam of a plurality of soft-electronic beams, and wherein the plurality of soft-electronic beams form a three-dimensional structure that conforms to the anatomical structure responsive to receiving the fluid.

3. The device of claim 2, wherein the three-dimensional structure formed by the plurality of soft-electronic beams is at least one of a star configuration, a sphere configuration, a linear configuration, a conical configuration, or a cylindrical configuration.

4. The device of claim 1, wherein at least one of the first polymer or the second polymer comprise at least one of a urethane polymer, a polyurethane polymer, a copolymer, a silicone polymer, or an elastomer.

5. The device of claim 1, wherein the conductive trace provides the signal detected by the conductive pad to a catheter that transmits the signal to an external measurement device.

6. The device of claim 1, wherein the conductive trace is coupled to a portion of a flexible printed-circuit board substrate that is coupled to at least one of the first polymer substrate or the second polymer substrate.

7. The device of claim 1, wherein one or more of the conductive pad or the conductive trace is electrically coupled to a sensor comprising at least one of a force sensor, a shear sensor, an ultrasound senor, a thermal sensor, a position sensor, an electrocardiogram sensor, or an electrochemical sensor.

8. The device of claim 7, wherein the sensor is coupled to at least one of the first polymer substrate, the second polymer substrate, or a flexible printed-circuit board layer coupled to the conductive layer and to at least one of the first polymer substrate or the second polymer substrate.

9. The device of claim 7, wherein the second polymer substrate is coupled to a second conductive trace electrically coupled to a second conductive pad; and wherein the second conductive pad is coupled to a second sensor comprising at least one of a force sensor, a shear sensor, an ultrasound senor, a thermal sensor, a position sensor, an electrocardiogram sensor, or an electrochemical sensor.

10. The device of claim 1, wherein the conductive trace is patterned in at least one of a serpentine pattern, a linear pattern, a curved pattern, or a zig-zag pattern, wherein the conductive trace stretches in response to the first inlet portion receiving the fluid that expands the first cavity.

11. A method of detecting signals using an expandable measurement device, comprising:
   positioning a measurement device within an internal anatomical structure of a patient, the measurement device comprising:
      a first polymer substrate having a first surface coupled to a conductive layer forming a conductive trace electrically coupled to a conductive pad exposed through a second surface of the first polymer substrate via an opening in the first polymer substrate;
      a second polymer substrate secured to the first polymer substrate and forming a first cavity between the first polymer substrate and the second polymer substrate; and
      a first inlet portion coupled to a lumen that receives a fluid that expands the first cavity;
   providing, via the lumen, a first amount of the fluid that causes the measurement device to expand by a volume corresponding to the first amount of fluid, wherein the conductive pad detects a signal from the internal anatomical structure via the opening responsive to expanding the first cavity; and
   monitoring, responsive to providing the first amount of the fluid via the lumen, using a measurement device, the signal detected by the conductive pad.

12. The method of claim 11, further comprising:
   determining that the signal from the internal anatomical structure is not detected by the conductive pad responsive providing the first amount of the fluid; and
   providing, responsive to the determination that the signal is not detected, a second amount of the fluid that causes the cavity to a size larger than the size of the cavity after providing the first amount of the fluid.

13. The method of claim 11, wherein monitoring the signal using the measurement device further comprises measuring at least one of a force value, a shear force value, an ultrasound value, a temperature value, a position value, an electrocardiogram value, or an electrochemical value.

14. The method of claim 11, wherein providing the first amount of fluid comprises determining the first amount of the fluid based on at least one of a type of the internal anatomical structure, a volume of the measurement device, or information from an image of the internal anatomical structure.

15. The method of claim 11, wherein the internal anatomical structure is an atrium of a heart of the patient, and wherein positioning the measurement device within the internal tissue structure is performed using at least a transseptal puncture.

* * * * *